United States Patent
Iino et al.

(10) Patent No.: US 8,609,699 B2
(45) Date of Patent: Dec. 17, 2013

(54) OXOTETRAHYDROFURAN-2-YL-BENZIMIDAZOLE DERIVATIVE

(75) Inventors: Tomoharu Iino, Koto-Ku (JP); Masanori Asai, Tsukuba (JP); Akio Ohno, Machida (JP); Seiichi Inamura, Yokohama (JP); Makoto Ishikawa, Susono (JP); Norikazu Ohtake, Tsukuba (JP)

(73) Assignee: MSD K.K., Tokyo (JP)

( * ) Notice: Subject to any disclaimer, the term of this patent is extended or adjusted under 35 U.S.C. 154(b) by 199 days.

(21) Appl. No.: 13/059,307

(22) PCT Filed: Aug. 3, 2009

(86) PCT No.: PCT/JP2009/064072
§ 371 (c)(1),
(2), (4) Date: Feb. 16, 2011

(87) PCT Pub. No.: WO2010/024110
PCT Pub. Date: Mar. 4, 2010

(65) Prior Publication Data
US 2011/0144162 A1    Jun. 16, 2011

Related U.S. Application Data

(60) Provisional application No. 61/196,500, filed on Oct. 17, 2008.

(30) Foreign Application Priority Data

Aug. 29, 2008   (JP) .................................. 2008-220952

(51) Int. Cl.
*A61K 31/4439*   (2006.01)
*C07D 401/14*    (2006.01)

(52) U.S. Cl.
USPC ........................................ 514/338; 546/273.4

(58) Field of Classification Search
USPC ........................................ 546/273.4; 514/338
See application file for complete search history.

(56) References Cited

U.S. PATENT DOCUMENTS

| | | |
|---|---|---|
| 2006/0167053 A1 | 7/2006 | Iino et al. |
| 2006/0258701 A1 | 11/2006 | Mitsuya et al. |
| 2008/0070928 A1 | 3/2008 | Nonoshita et al. |
| 2008/0090799 A1 | 4/2008 | Hashimoto et al. |
| 2008/0125429 A1 | 5/2008 | Hashimoto et al. |
| 2009/0018056 A1 | 1/2009 | Iino et al. |
| 2009/0118304 A1 | 5/2009 | Takahashi et al. |
| 2010/0041660 A1 | 2/2010 | Mitsuya et al. |

FOREIGN PATENT DOCUMENTS

| | | |
|---|---|---|
| WO | 2007/007910 | 1/2007 |
| WO | 2010/107610 | 9/2010 |

OTHER PUBLICATIONS

Vionnet et al., "Nonsense mutation in the glucokinase gene causes early-onset non-insulin-dependent diabetes meilitus", Nature (1992), vol. 356, pp. 721-722.
Glaser et al., "Familial hyperinsulinism caused by an activating glucokinase mutation", New England J. of Medicine (1998), vol. 338, pp. 226-230.
Ferre et al., "Correction of diabetic aiterations by glucokinase", PNAS (1996), vol. 93, pp. 7225-7230.
Grupe et al., "Transgenic knockouts reveal a critical requirement for pancreatic beta cell glucokinase . . . ", Cell (1995), vol. 83, pp. 69-78.
Garfinkel et al., "Computer modeling identifies glucokinaso as glucose sensor of pancreatic beta cells", Am. J. Physiol. (1984), vol. 247, pp. R527-R536.
Int'l Search Report of PCT/JP2009/064072, dated Sep. 29, 2009.
Int'l Preliminary Report on Patentability of PCT/JP2009/064072, dated Mar. 1, 2011.

*Primary Examiner* — Patricia L Morris
(74) *Attorney, Agent, or Firm* — Anna L. Cocuzzo; Catherine D. Fitch

(57) ABSTRACT

The present invention relates to compounds, which are useful for treatment and/or prevention of diabetes mellitus, diabetes mellitus complications or obesity, since the compounds have glucokinase-activating effects, and are presented in Formula (I): wherein R1 represents a carbamoyl group; R2 represents a lower alkyl group; both of X1 and X2 represent CH, or any one of X1 and X2 represents a nitrogen atom and the other represents CH; a group of represents a group selected from the group consisting of a pyridinyl, a pyrazinyl, a pyrazolyl, a thiadiazolyl, a triazolyl, an isoxazolyl and a thiazolyl group; and k is zero or 1, or relates to pharmaceutically acceptable salts thereof.

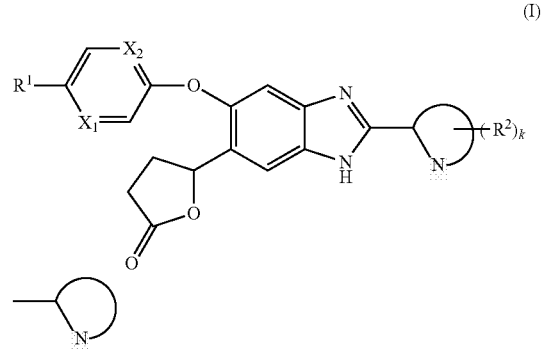

10 Claims, No Drawings

OXOTETRAHYDROFURAN-2-YL-BENZIMIDAZOLE DERIVATIVE

TECHNICAL FIELD

The present invention relates to glucokinase activators comprising an oxotetrahydrofuran-2-yl-benzimidazoles as an active ingredient thereof. The present invention further relates to a novel oxotetrahydrofuran-2-yl-benzimidazole derivative.

BACKGROUND ART

Glucokinase (gk) (atp: d-hexose 6-phosphotransferaze, ec 2.7.1.1) is one (hexokinase IV) of four mammal hexokinases. Hexokinase is a first-stage enzyme in glycolysis and catalyzes a reaction from glucose to glucose hexaphosphate. In its expression, glucokinase is limited essentially in liver and pancreas beta cells, and it controls the rate-limiting step of glucose metabolism in these cells thereby playing an important role in systemic saccharometabolism. Glucokinase in liver and that in pancreas beta cells differ from each other in point of the N-terminal 15-amino acid sequence owing to the difference in splicing therebetween, but they are the same in point of the enzymatic property. The enzymatic activity of the other three hexokinases (I, II, III) except glucokinase is saturated at a glucose concentration of at most 1 mM, but Km of glucokinase to glucose is 8 mM and is near to a physiological blood-glucose level. Therefore, in accordance with the blood-glucose level change from a normal blood-glucose level (5 mM) to an increased blood-glucose level after meals (10 to 15 mM), intercellular glucose metabolism is accelerated via glucokinase.

Since ten years ago, a hypothesis that glucokinase may act as a glucose sensor in pancreas beta cells and liver has been proposed (for example, see Garfinkel D, et al., "Computer modeling identifies glucokinase as glucose sensor of pancreatic beta-cells", American Journal Physiology, Vol. 247 (3Pt2), 1984, pp. 527-536). A result of recent glucokinase gene-manipulated mice has confirmed that glucokinase actually plays an important role in systemic glucose homeostasis. Mice in which the glucokinase gene was disrupted die soon after their birth (for example, see Grupe A. et al., "Transgenic knockouts reveal a critical requirement for pancreatic beta cell glucokinase in maintaining glucose homeostasis", Cell, Vol. 83, 1995, pp. 69-78), but on the other hand, normal or diabetic mice in which glucokinase was excessively expressed have a lowered blood-glucose level (for example, see Ferre T. et al., "Correction of diabetic alterations by glucokinase", Proceedings of the National Academy of Sciences of the U.S.A., Vol. 93, 1996, pp. 7225-7230).

With the increase in glucose concentration therein, the reaction of pancreas beta cells and that of liver cells are both toward the reduction in a blood-glucose level, though differing from each other. Pancreas beta cells come to secrete more insulin, and liver takes up sugar to store it as glycogen therein and simultaneously reduces glucose release.

To that effect, the change in the enzymatic activity of glucokinase plays an important role in mammal glucose homeostasis via liver and pancreas beta cells. In a juvenile diabetic case that is referred to as MODY2 (maturity-onset diabetes of the young), mutation of a glucokinase gene has been found, and the glucokinase activity reduction causes the blood-glucose level increase (for example, see Vionnet N. et al., "Nonsense mutation in the glucokinase gene causes early-onset non-insulin-dependent diabetes mellitus", Nature Genetics, Vol. 356, 1992, pp. 721-722). On the other hand, a pedigree having mutation of increasing glucokinase activity has been found, and those of the family line show low blood-glucose level symptoms (for example, Glaser B. et al., "Familial hyperinsulinism caused by an activating glucokinase mutation", New England Journal Medicine, Vol. 338, 1998, pp. 226-230).

From these, glucokinase acts as a glucose sensor and plays an important role in glucose homeostasis also in humans. On the other hand, blood-glucose level control by utilizing a glucokinase sensor system may be possible in many type-II diabetes patients. A glucokinase-activating substance may be expected to have an insulin secretion promoting effect in pancreas beta cells and have a sugar take-up accelerating and sugar release inhibiting activity in liver, and therefore it may be useful as a remedy for type-II diabetes patients.

Recently, it has become clarified that pancreas beta cell-type glucokinase is limitedly expressed locally in rat brains, especially in ventromedial hypothalamus (VMH) thereof. About 20% neurocytes in VMH are referred to as glucose-responsive neutrons, and heretofore it has been considered they may play an important role in body weight control. When glucose is administered to a rat brain, then it reduces the amount of ingestion; but when glucose metabolism is retarded through intracerebral administration of glucosamine, a glucose analogue, then it causes hyperphagia. From an electrophysiological experiment, it is admitted that glucose-responsive neurons are activated in accordance with a physiological glucose concentration change (5 to 20 mM), but when glucose metabolisms is inhibited by glucosamine or the like, then their activity is retarded. In the glucose concentration-sensitive system in VMH, a glucose-mediated mechanism is anticipated like the insulin secretion in pancreas beta cells. Accordingly, there may be a possibility that a substance for glucokinase activation in VMH, in addition to liver and pancreas beta cells, may be effective not only for blood-glucose level correction but also for solution of obesity that is problematic in many type-II diabetes patients.

From the above description, a compound having a glucokinase-activating effect is useful for remedies and/or preventives for diabetes, or for remedies and/or preventives for chronic complications of diabetes such as retinopathy, nephropathy, neurosis, ischemic cardiopathy, arteriosclerosis, and further for remedies and/or preventives for obesity.

Compounds that have glucokinase-activating effects and a benzimidazole skeleton, including a compound presented in Formula (I) shown below, are disclosed in WO 2007/007910.

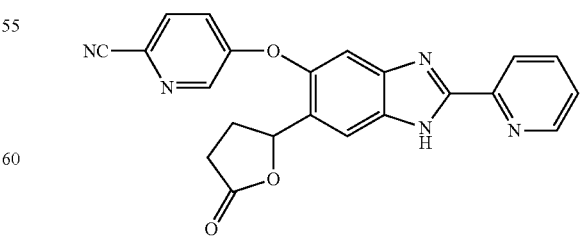

WO 2007/007910 discloses that the above-mentioned compounds having a benzimidazole skeleton or the like have adequate glucokinase-activating effects in a racemate.

DISCLOSURE OF THE INVENTION

The present invention is directed to provide a novel compound having a glucokinase-activating effect.

As a result of diligent research, we, the present inventors have assiduously studied and have found that a compound of Formula (I) shown below, or a pharmaceutically acceptable salt thereof has an adequate glucokinase-activating effect and high solubility in water, and the invention has been completed on the basis of this finding.

Specifically, the present invention is:

(1) to provide a compound, presented in Formula (I) shown below, or a pharmaceutically acceptable salt thereof (hereinafter also referred to as "compound according to the present invention" or "compound presented in Formula (I)"):

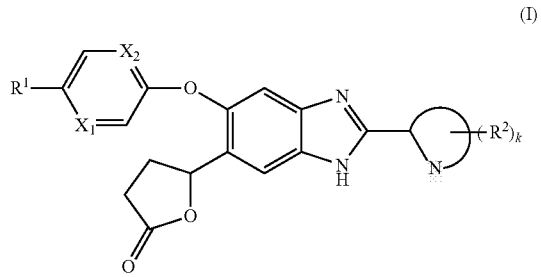

wherein $R^1$ is Formula (II):

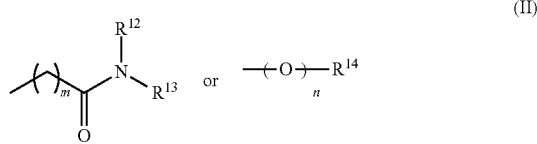

wherein $R^{12}$ and $R^{13}$ each independently represent a hydrogen atom or a lower alkyl group, or $R^{12}$ and $R^{13}$ together with a nitrogen atom to which they are attached represent an azetidin-1-yl group, a pyrrolidine-1-yl group, a piperidine-1-yl group, or a homopiperidine-1-yl group;
$R^{14}$ represents a lower alkyl group optionally having 1 to 4 the same or different hydroxy groups, lower alkoxy groups or halogen atoms;
m represents zero or 1;
n represents zero or 1;
both of $X_1$ and $X_2$ represent CH, or any one of $X_1$ and $X_2$ represents a nitrogen atom and the other represents CH; and
a group of Formula (IV):

represents a group selected from the group consisting of a pyridinyl, a pyrazinyl, a pyrazolyl, a thiadiazolyl, a triazolyl, an isoxazolyl, and a thiazolyl groups;
$R^2$ represents a lower alkyl group optionally substituted with a hydroxy group, a lower alkoxy group, or a hydroxy group; and
k represents zero or 1.

Furthermore, the present invention is also:

(2) to provide pharmaceutical compositions for treatment, prevention and/or delay of onset of type 2 diabetes, comprising the following (α) to (γ):
(α) a compound of the aforementioned formula (I);
(β) one or more compounds selected from the group consisting of the following (a) to (i):
(a) other glucokinase activators;
(b) biguanides;
(c) PPAR agonists;
(d) insulin;
(e) somatostatins;
(f) α-glucosidase inhibitors;
(g) insulin secretagogues;
(h) DPP-IV inhibitors (dipeptidyl peptidase inhibitors); and
(i) glucose uptake facilitators; and
(γ) pharmacologically acceptable carriers;

(3) to provide a glucokinase activator comprising a compound of the aforementioned formula (I), or a pharmaceutically acceptable salts thereof as an active ingredient;

(4) to provide an agent for treating and/or preventing diabetes comprising a compound of the aforementioned formula (I), or a pharmaceutically acceptable salts thereof as an active ingredient; and (5) to provide a pharmaceutical composition comprising a compound of the aforementioned formula (I), or a pharmaceutically acceptable salts thereof as an active ingredient.

Since the compounds of the aforementioned formula (I) has glucokinase-activating effects, they are useful as an agent for treating and/or preventing diabetes, as an agent for treating and/or chronic complications of diabetes, such as retinopathy, nephropathy, neurosis, ischemic heart disease and arteriosclerosis, and further as an agent for treating and/or preventing obesity.

The compounds of the aforementioned formula (I) are useful preferably as an agent for treating and/or preventing diabetes, further preferably as an agent for diabetes.

The meanings of the terms used herein are described, and the compounds of the present invention are described in more detail.

"Lower alkyl group" means a linear or branched alkyl group having from 1 to 6 carbon atoms, including, for example, a methyl group, an ethyl group, a propyl group, an isopropyl group, a butyl group, an isobutyl group, a sec-butyl group, a tert-butyl group, a pentyl group, an isoamyl group, a neopentyl group, an isopentyl group, a 1,1-dimethylpropyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,2,2-trimethylpropyl group, a 1-ethyl-2-methylpropyl group. "Lower alkoxy group" means a hydroxyl group of which the hydrogen atom is substituted with the above-mentioned lower alkyl group, and includes, for example, a methoxy group, an ethoxy group, a propoxy group, an isopropoxy group, a butoxy group, a sec-butoxy group, a tert-butoxy group, a pentyloxy group, an isopentyloxy group, a hexyloxy group, an isohexyloxy group.

"Halogen atom" means, e.g., a fluorine atom, a chlorine atom, a bromine atom, or an iodine atom.

In order to more specifically disclose compounds of Formula (I) according to the present invention:

Formula (I)

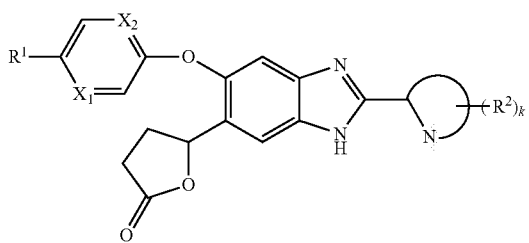

(I)

wherein the symbols have the same meanings as above and the symbols used in Formula (I) are described with reference to specific examples.

$R^1$ represents a group of Formula (II):

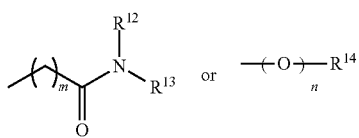

(II)

$R^{12}$ and $R^{13}$ independently represent a hydrogen atom or a lower alkyl group, or $R^{12}$ and $R^{13}$ together with a nitrogen atom to which they are attached represent an azetidin-1-yl group, a pyrrolidine-1-yl group, a piperidine-1-yl group, or a homopiperidine-1-yl group.

"Lower alkyl groups" for $R^{12}$ and $R^{13}$ have the same meanings as "lower alkyl groups" defined above, specifically, examples of which include a methyl, an ethyl, a n-propyl, and an isopropyl group.

$R^{12}$ and $R^{13}$ may be the same or different, where they are a hydrogen atom or a lower alkyl group.

m represents zero or 1, preferably, m is 1.

A Group of Formula (II-2):

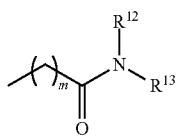

(II-2)

in the aforementioned formula (II) includes, specifically, e.g., an azetidin-1-ylcarbonyl, a N,N-diethylcarbamoyl, a N,N-dimethylcarbamoyl, a N-ethyl-N-methylcarbamoyl, a N-ethylcarbamoyl, a N,N-dimethylcarbamoylmethyl, a N-methylcarbamoylmethyl, and an azetidin-1-ylcarbonylmethyl group.

$R^{14}$ represents a lower alkyl group, which may has the same or different, 1 to 4 hydroxy groups, lower alkoxy groups or halogen atoms.

"Lower alkyl group optionally having the same or different, 1 to 4 hydroxy groups, lower alkoxy groups or halogen atoms" for $R^{14}$ represents a lower alkyl group which is unsubstituted or substituted with the same or different, 1 to 4 groups selected from the group consisting of hydroxy groups, lower alkoxy groups and halogen atoms.

The unsubstituted lower alkyl group means a group identical to the lower alkyl group defined above, specifically, examples of which include a methyl, an ethyl, a n-propyl, and an isopropyl group.

The lower alkoxy group of the substituted group means a group identical to the lower alkoxy group defined above, specifically, examples of which include methoxy, ethoxy, n-propoxy, and isopropoxy group.

The halogen atom of the substituent group means an atom identical to the halogen atom defined above, specifically, e.g., a fluorine atom, a chlorine atom, a bromine atom or an iodine atom.

A group of Formula:

in the aforementioned formula (II) includes, specifically, e.g., a 2,2,2-trifluoro-1-hydroxyethyl, a 2-hydroxyethoxy, a methoxymethyl, a hydroxymethyl, and a 1-hydroxyethyl group.

Both of $X_1$ and $X_2$ represent CH, or any one of $X_1$ and $X_2$ represents a nitrogen atom and the other represents CH.

A group of Formula (IV):

(IV)

in Formula (I) represents a group selected from the group consisting of a pyridinyl, a pyrazinyl, a pyrazolyl, a thiadiazolyl, a triazolyl, an isoxazolyl and a thiazolyl group, specifically, represents a group selected from the group consisting of Formulas:

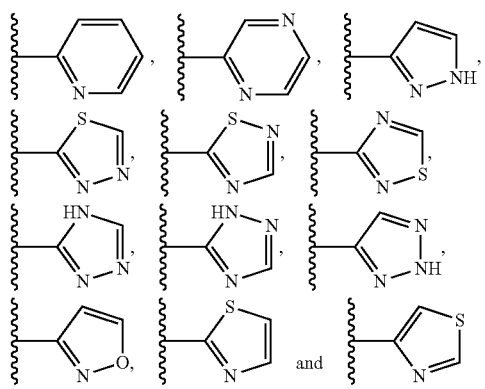

wherein

ξ shows a site attached to a benzimidazole ring.

$R^2$ represents a lower alkyl group optionally substituted with a hydroxy group, a lower alkoxy group, or a hydroxy group.

"Lower alkyl group optionally substituted with a hydroxy group" for $R^2$ means a lower alkyl group, unsubstituted or substituted with a hydroxy group.

The unsubstituted lower alkyl group means a group identical to the lower alkyl group defined above, specifically, examples of which include a methyl, an ethyl, a n-propyl, and an isopropyl group.

The lower alkyl groups substituted with a hydroxy group means the above-mentioned lower alkyl group substituted with a hydroxy group, specifically, examples of which include a hydroxymethyl, a 1-hydroxyethyl, a 2-hydroxyethyl, a 3-hydroxypropyl, and a 1-hydroxy-1-methylethyl group.

"Lower alkoxy group" for $R^2$ means a group identical to the "lower alkoxy group" defined above, specifically, examples of which include a methoxy, an ethoxy, a propoxy, and an isopropoxy group.

k represents zero or 1.

(A) Another preferred embodiment of a compound according to the present invention is a compound or a pharmaceutically acceptable salt thereof, in which a group of Formula:

$$\text{\textsection}\!\!-\!\!\underset{X_1=\!\!=\!\!}{\overset{X_2}{\bigcirc}}\!\!-\!\!\text{\textsection}$$

wherein

§ shows sites attached to $R^1$ and an oxygen atom and the other symbols have the same meanings as above, in the aforementioned formula (I), is a divalent group having a benzene ring, from which two hydrogen atoms are removed, in the aforementioned formula (I).

(B) Another preferred embodiment of a compound according to the present invention is a compound or a pharmaceutically acceptable salt thereof, in which a group of Formula:

$$\text{\textsection}\!\!-\!\!\underset{X_1=\!\!=\!\!}{\overset{X_2}{\bigcirc}}\!\!-\!\!\text{\textsection}$$

wherein

§ shows sites attached to $R^1$ and an oxygen atom and the other symbols have the same meanings as above, in the aforementioned formula (I), is a divalent group having a pyridine ring with $X_1$ as a nitrogen atom, from which two hydrogen atoms are removed, in the aforementioned formula (I).

(C) Another preferred embodiment of a compound according to the present invention is also the compound according to the aforementioned (A) or (B) or a pharmaceutically acceptable salt thereof, in which $R^1$ is a group of Formula (II-2):

$$\text{(II-2)}$$

wherein the symbols have the same meanings as above.

(D) Another preferred embodiment of a compound according to the present invention is also the compound according to the aforementioned (A) or (B) or a pharmaceutically acceptable salt thereof, in which $R^1$ is a group of Formula (II-3):

—$R^{14}$ (II-3)

wherein $R^{14}$ has the same meaning as above.

(E) Another preferred embodiment of a compound according to the present invention is also the compound according to the aforementioned (A) or (B) or a pharmaceutically acceptable salt thereof, in which $R^1$ is an azetidin-1-ylcarbonyl group, a dimethylcarbamoylmethyl group, a methylcarbamoylethyl group, or an ethylcarbamoyl group.

(F) Another preferred embodiment of a compound according to the present invention is also the compound according to the aforementioned (A) or (B) or a pharmaceutically acceptable salt thereof, in which $R^1$ is a methoxymethyl group.

(G) Another preferred embodiment of a compound according to the present invention is also the compound according to the aforementioned (A) or (B) or a pharmaceutically acceptable salt thereof, in which $R^1$ is a dimethylcarbamoylmethyl group or a methylcarbamoylmethyl group.

(H) Another preferred embodiment of a compound according to the present invention is also the compound according to any one of the aforementioned (1) and (A) to (C) or a pharmaceutically acceptable salt thereof, in which m is 1.

(I) Another preferred embodiment of a compound according to the present invention is also the compound according to any one of the aforementioned (E) to (H) or a pharmaceutically acceptable salt thereof, in which a group of the aforementioned formula (IV) is a group selected from the group consisting of a pyridinyl group, a pyrazinyl group, and a thiazolyl group.

(J) Another preferred embodiment of a compound according to the present invention is also the compound according to any one of the aforementioned (1) and (A) to (I) or a pharmaceutically acceptable salt thereof, in which k is zero.

(K) In another preferred embodiment of a compound according to the present invention, a compound presented in the aforementioned formula (I) is a compound selected from the group consisting of 5-{5-[4-(azetidin-1-ylcarbonyl)phenoxy]-2-pyridin-2-yl-1H-benzimidazol-6-yl}dihydrofuran-2(3H)-one, 5-(5-{[6-(azetidin-1-ylcarbonyl)pyridin-3-yl)oxy}-2-pyridin-2-yl-1H-benzimidazol-6-yl)dihydrofuran-2(3H)-one, N,N-diethyl-5-{[6-(5-oxotetrahydrofuran-2-yl)-2-pyridin-2-yl-1H-benzimidazol-5-yl]oxy}pyridine-2-carboxamide, N,N-dimethyl-5-{[6-(5-oxotetrahydrofuran-2-yl)-2-pyridin-2-yl-1H-benzimidazol-5-yl]oxy}pyridine-2-carboxamide, N-ethyl-N-methyl-5-{[6-(5-oxotetrahydrofuran-2-yl)-2-pyridin-2-yl-1H-benzimidazol-5-yl]oxy}pyridine-2-carboxamide, N-ethyl-5-{[6-(5-oxotetrahydrofuran-2-yl)-2-pyridin-2-yl-1H-benzimidazol-5-yl]oxy}pyridine-2-carboxamide, N,N-dimethyl-2-(4-{[6-(5-oxotetrahydrofuran-2-yl)-2-pyridin-2-yl-1H-benzimidazol-5-yl]oxy}phenyl)acetamide, N-methyl-2-(4-{[6-(5-oxotetrahydrofuran-2-yl)-2-pyridin-2-yl-1H-benzimidazol-5-yl]oxy}phenyl)acetamide, 5-(2-pyridin-2-yl-5-{[6-(2,2,2-trifluoro-1-hydroxyethyl)pyridin-3-yl]oxy}-1H-benzimidazol-6-yl)dihydrofuran-2(3H)-one, 5-(5-{[6-(2-hydroxyethoxy)pyridin-3-yl]oxy}-2-pyridin-2-yl-1H-benzimidazol-6-yl)dihydrofuran-2(3H)-one, 5-(5-{[6-(methoxymethyl)pyridin-3-yl]oxy}-2-pyridin-2-yl-1H-benzimidazol-6-yl)dihydrofuran-2(3H)-one, and 5-(5-{[5-(methoxymethyl)pyridin-2-yl]oxy}-2-pyridin-2-yl-1H-benzimidazol-6-yl)dihydrofuran-2(3H)-one; or a pharmaceutically acceptable salt thereof.

All of the compounds or pharmaceutically acceptable salts thereof of the aforementioned (A) to (L) are encompassed in the compounds of the aforementioned formula (I), or the pharmaceutically acceptable salts thereof.

A compound of Formula (I) according to the present invention:

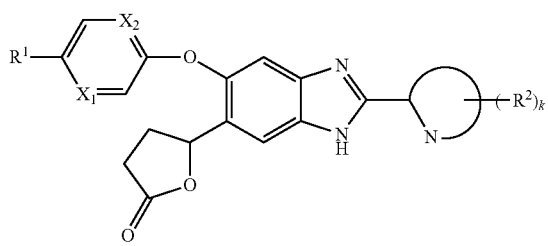

wherein the symbols have the same meanings as above, respectively, may be produced, e.g., by the following process:

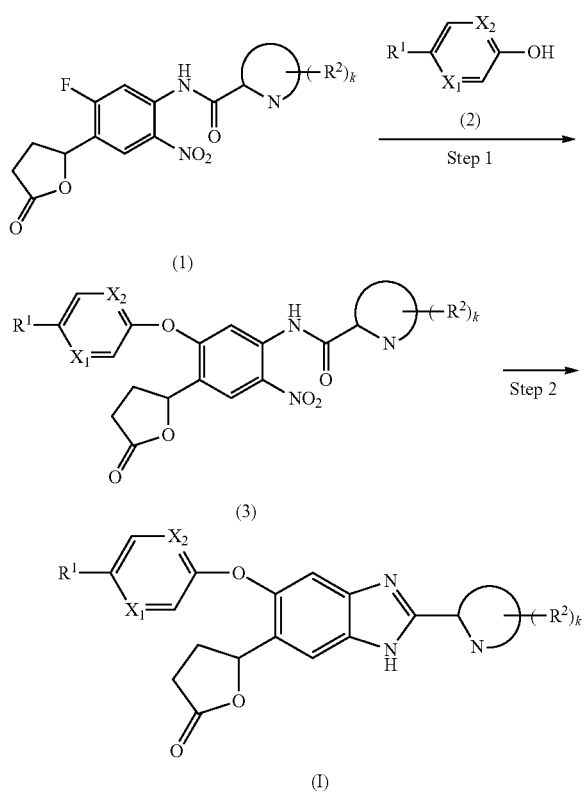

wherein the symbols have the same meanings as above, respectively.

(Step 1)

This step is a process of producing a compound (3) by reacting a compound (1) with a compound (2) in the presence of a base.

The compound (1) used in this step can be produced by the method described in the literature (steps 1 to 5 in Example 20 in WO 2007/007910), methods similar thereto, or combinations of them and usual methods, using a carboxylic acid derivative of Formula:

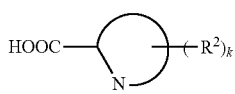

wherein the symbols have the same meanings as above, respectively.

The amount of compound (2) used in this step are usually 0.5 to 10 equivalents, and, preferably an 1 to 2 equivalents, relative to 1 equivalent of the compound (1).

The compound (2) is commercially available thing or may be manufactured from commercially available materials by processes known to those skilled in the art or processes similar thereto. Examples of bases used in this step include potassium carbonate, sodium carbonate, cesium carbonate, triethylamine, and cesium fluoride.

The base are usually 0.5 to 20 equivalents, and, preferably 1 to 5 equivalents, relative to 1 equivalent of the compound (1).

Reaction solvents include, but are not particularly limited unless impeding the reaction, N-methylpyrrolidone, N,N-dimethylformamide, tetrahydrofuran, and acetonitrile, among which N-methylpyrrolidone and N,N-dimethylformamide are preferred.

Reaction time is usually one minute to 72 hours, preferably 10 minutes to 12 hours.

Reaction temperature is normally room temperature to the boiling point of a solvent, preferably room temperature to 130° C.

A compound (3) provided in such a manner may be isolated and purified by well-known separation and purification means, such as concentration, vacuum concentration, reprecipitation, solvent extraction, crystallization or chromatography, or may be subjected to the subsequent step without isolation and purification.

(Step 2)

This step is a process of producing a compound (1) according to the present invention by reducing the compound (3) to its elements and further cyclizing them.

Examples of reducing agents used in this step include stannous chloride(II), iron (II), Raney nickel, and palladium hydroxide.

The amount of the reducing agent are usually 0.01 to 50 equivalents, and, preferably 0.1 to 20 equivalents, relative to 1 equivalent of the compound (3).

Reaction solvents include, but are not particularly limited unless impeding the reaction, water, methanol, ethanol, N-methylpyrrolidone, N,N-dimethylformamide, tetrahydrofuran, and acetic acid.

Reaction time is usually one minute to 24 hours, preferably 5 minutes to 12 hours.

Reaction temperature is usually zero to 150° C., preferably room temperature to 120° C.

The compound (1) provided in such a manner may be isolated and purified by well-known separation and purification means, such as concentration, vacuum concentration, reprecipitation, solvent extraction, crystallization or chromatography.

In the above-mentioned reaction, the protective group may be introduced or removed in any desired manner. Concretely, the introduction or removal of the protective group may be attained in the same manner as in the method described in literature (for example, Protective Groups in Organic Synthesis, by T. W. Green, 2nd Ed., John Wiley & Sons, 1991), or in accordance with it, or by combining it with an ordinary method.

The oxotetrahydrofuran-2-yl-benzimidazole derivative provided by the present invention may be present as a pharmaceutically acceptable salt, which may be produced according to a usual method using a compound presented in Formula (I) or compounds encompassed in Formula (I).

Specifically, the above-mentioned compounds according to or encompassed in Formula (I), when having basic groups derived from, e.g., an amino or pyridyl group, in the molecule, can be converted into corresponding pharmaceutically acceptable salts by treatment of the compounds with acid.

The acid-addition salts include, for example, hydrohalides such as hydrochlorides, hydrofluorides, hydrobromides, hydroiodides; inorganic acid salts such as nitrates, perchlorates, sulfates, phosphates, carbonates; lower alkylsulfonates such as methanesulfonates, trifluoromethanesulfonates, ethanesulfonates; arylsulfonates such as benzenesulfonates, p-toluenesulfonates; organic acid salts such as fumarates, succinates, citrates, tartrates, oxalates, maleates; other organic acid-addition salts with amino acid such as glutamates, aspartates. When the compounds of the invention have an acid group in the molecule, for example, when they have a carboxyl group, then the compounds may be processed with a base so as to convert them into the corresponding pharmaceutically-acceptable salts. The base-addition salts include, for example, alkali metal salts with sodium or potassium; alkaline earth metal salts with calcium or magnesium; ammonium salts; organic base-addition salts with guanidine, triethylamine, dicyclohexylamine, etc. In addition, the compounds of the invention may also be in any other form of hydrates or solvates of their free compounds or their salts.

Depending on the type of the substituents therein, the compounds of the invention include stereoisomers and tautomers such as optical isomers, diastereomeric isomers and geometrical isomers. Needless-to-say, the compounds of the invention include all these isomers. Further needless-to-say, the compounds of the invention include all mixtures of such isomers.

In producing medicines for prevention and remedy for type II diabetes or diseases or symptoms associated with it, the compounds of formula (I) of the invention may be combined with carrier substances.

Needless to mention, the administered dosage for prevention or treatment of a compound of Formula (I) according to the present invention varies depending on the nature of the condition to be treated, the specific compound selected, and the route of administration.

In addition, the dose also varies depending on the age, the body weight and the sensitivity of patients. In general, the daily dose for one-time or plural-times administration may be from about 0.001 mg/kg-body weight to about 100 mg/kg-body weight, preferably from about 0.01 mg/kg-body weight to about 50 mg/kg-body weight, even more preferably from about 0.1 mg/kg-body weight to about 10 mg/kg-body weight. As the case may be, administration of a dose over the range may be necessary.

An example of a suitable dose for oral administration is described. The daily dose for one-time or two- to four-times administration may be at least from about 0.01 mg to at most 2.0 g. Preferably, the daily administration frequency is once or twice a day, and the daily dose is from about 1.0 mg to about 200 mg. More preferably, the daily dose is from about 10 mg to 100 mg for one-time administration a day.

For intravenous administration or oral administration, a typical dose of the compound (1) may be from about 0.001 mg/day/kg-body weight to about 100 mg/day/kg-body weight (preferably from 0.01 mg/day/kg-body weight to about 10 mg/day/kg-body weight), more preferably from about 0.1 mg/day/kg-body weight to 10 mg/day/kg-body weight.

As mentioned above, the pharmaceutical composition contains a compound of Formula (I) and a pharmaceutically acceptable carrier. The term "composition" includes active and inactive components (pharmaceutically acceptable excipients) composing the carrier, as well as a product obtained by directly or indirectly combining, compounding or aggregating two or more components, a product obtained as a result of dissociation of one or more components, or a product obtained as a result of any other type of action or interaction between components.

As combined with a pharmaceutically-acceptable carrier, the composition of the invention preferably contains a compound of formula (I) in an amount effective for treatment and prevention of type II diabetes and for delay of the onset of the disease.

For administering the effective dose of the compound of the invention to mammals, especially to humans, employable is any suitable administration route. For example, the route may be oral administration, rectal administration, local administration, intravenous administration, ophthalmic administration, lung administration or nasal administration. Examples of the administration forms are tablets, troches, powders, suspensions, solutions, capsules, creams, aerosols. Preferred are oral tablets.

In preparing oral compositions, usable are any ordinary pharmaceutical media. Their examples are water, glycol, oil, alcohol, fragrant additives, preservatives, colorants. In preparing liquid compositions for oral administration, for example, mentioned are suspensions, elixirs and solutions. Their carriers are, for example, starch, sugar, microcrystalline cellulose, diluent, granulating promoter, lubricant, binder, disintegrator. In preparing solid compositions for oral administration, for example, mentioned are powders, capsules and tablets. Above all, such solid compositions for oral administration are preferred.

In view of the easiness in their administration, tablets and capsules are the most advantageous forms for oral administration. If desired, the tablets may be coated according to standard aqueous or non-aqueous coating techniques.

In addition to the above-mentioned ordinary administration modes for them, the compounds of formula (I) may also be administered according to controlled release systems and/or controlled delivery systems, for example, as in U.S. Pat. Nos. 3,845,770, 3,916,899, 3,536,809, 3,598,123, 3,630,200 and 4,008,719.

The pharmaceutical composition of the invention suitable for oral administration includes capsules, cashews and tablets that contain a predetermined amount of the active ingredient in the form of powders or granules thereof, or in the form of water-soluble liquids, water-insoluble liquids, oil-in-water emulsions or water-in-oil emulsions thereof. These compositions may be prepared in any pharmaceutical methods, and all the methods include a process of combining the active ingredient with a carrier of one or more necessary ingredients.

In general, the active ingredient is uniformly and fully mixed with a liquid carrier, or a well-separated solid carrier or with both the two, and then, if desired, the product is shaped into suitable forms to prepare the composition. For example, tablets are produced through compression and shaping, optionally along with one or more side components. Using a suitable machine, compressed tablets may be produced by mixing the active ingredient optionally with binder, lubricant, inert vehicle, surfactant or dispersant and compressing the resulting mix in any desired manner into powders or granules.

Shaped tablets may be prepared by shaping a mixture of a powdery wet compound and an inert liquid diluent, using a suitable machine.

Preferably, the tablets each contain from about 1 mg to 1 g of the active ingredient; and the cashews and the capsules each contain from about 1 mg to 500 mg of the active ingredient.

Examples of the administration modes of the compounds of formula (I) for pharmaceutical use are as follows:

TABLE 1

| Suspension for injection (I.M.) | mg/ml |
|---|---|
| Compound of Formula (I) | 10 |
| Methyl cellulose | 5.0 |
| Tween 80 | 0.5 |
| Benzyl alcohol | 9.0 |
| Benzalkonium chloride | 1.0 |
| Water for injection added to 1.0 ml | |

TABLE 2

| Tablets | mg/tablet |
|---|---|
| Compound of Formula (I) | 25 |
| Methyl cellulose | 415 |
| Tween 80 | 14.0 |
| Benzyl alcohol | 43.5 |
| Magnesium stearate | 2.5 |
| Total | 500 mg |

TABLE 3

| Capsules | mg/capsule |
|---|---|
| Compound of Formula (I) | 25 |
| Lactose powder | 573.5 |
| Magnesium stearate | 1.5 |
| Total | 600 mg |

TABLE 4

| Aerosol | per container |
|---|---|
| Compound of Formula (I) | 24 mg |
| Lecithin, NF Liq. Conc. | 1.2 mg |
| Trichlorofluoromethane, NF | 4.025 g |
| Dichlorodifluoromethane, NF | 12.15 g |

The compounds of formula (I) may be used, as combined with any other medicines usable not only for type II diabetes-associated diseases or symptoms but also for treatment/prevention/delay of the onset of type II diabetes. The additional medicines may be administered in any administration route and dose generally employed in the art, simultaneously with or separately from the compound of formula (I).

In case where the compound of formula (I) is used along with one or more other medicines, then a pharmaceutical composition comprising the compound of formula (I) and the additional medicines is preferred. Accordingly, the pharmaceutical composition of the invention may comprise not only the compound of formula (I) but also one or more such active ingredients. Examples of the active ingredients that may be combined with the compounds of formula (I) are mentioned below, which, however, are not limitative. These may be separately administered or may be administered simultaneously as contained in the same pharmaceutical composition.

(a) Other glucokinase activators,
(b) Bisguanides (e.g., buformin, metformin, phenformin)
(c) PPAR agonists (e.g., troglitazone, pioglitazone, rosiglitazone),
(d) insulin,
(e) somatostatin,
(f) α-glucosidase inhibitors (e.g., voglibose, miglitol, acarbose),
(g) insulin secretagogues (e.g., acetohexamide, carbutamide, chlorpropamide, glibomuride, gliclazide, glimerpiride, glipizide, gliquidine, glisoxepid, glyburide, glyhexamide, glypinamide, phenbutamide, tolazamide, tolbutamide, tolcyclamide, nateglinide, repaglinide), and
(h) DPP-IV (dipeptidyl peptidase IV inhibitor), and
(i) glucose uptake facilitators.

The weight ratio of the compound of formula (I) to the second active ingredient may vary within a broad range, and depends on the effective amount of the individual active ingredients. Accordingly, for example, when the compound of formula (I) is combined with a PPAR agonist, then the weight ratio of the compound of formula (I) to the PPAR agonist may be generally from about 1000/1 to 1/1000, preferably from about 200/1 to 1/200. The combination of the compound of formula (I) and the other active ingredient may be within the above-mentioned range. In any case, an effective amount of the individual ingredients should be in the combination.

The glucokinase-activating effect of a compound according to the present invention and antihyperglycemic effect based thereon are proved by, for example, pharmacological test examples described below.

Pharmacological Test Example 1

Glucokinase-Activating Effect

The glucokinase-activating potency of the compounds of formula (I) of the invention and a test method for it are described below.

The excellent glucokinase-activating effect of the compounds of formula (I) may be determined by a method described in literature (for example, Diabetes, Vol. 45, pp. 1671-1677, 1996), or in accordance with it.

The glucokinase activity may be determined not by directly measuring glucose-6-phosphate but by measuring the level of Thio-NADH, which is produced when a reporter enzyme, glucose-6-phosphate dehydrogenase produces phosphogluconolactone from glucose-6-phosphate, and based on the level, the degree of glucokinase activation by the compound tested may be determined.

In this assay, used was a recombinant human liver GK, which was expressed by E. coli as a FLAG fusion protein therein and was purified by ANTIFLAG M2 AFFINITY GEL (Sigma).

Using a flat-bottomed 96-well plate, the assay was carried out at 30° C. 69 μl of an assay buffer (25 mM Hepes Buffer/pH=7.2, 2 mM $MgCl_2$, 1 mM ATP, 0.5 mM TNAD, 1 mM dithiothreitol) was put into the plate, and 1 μl of a DMSO solution of the compound or DMSO alone as a control was added thereto. Next, 20 μl of an enzyme mixture (FLAG-GK, 20 U/ml G6PDH) cooled in ice was added to it, and 10 μl of a substrate, 25 mM glucose was added to it, and the reaction was initiated (final glucose concentration=2.5 mM).

After the start of the reaction, the increase in the absorbance at 405 nm was measured for 12 minutes at intervals of 30 seconds, and the increase for the first 5 minutes was used for assessing the compound tested. FLAG-GK was added so that the absorbance increase after 5 minutes in the presence of 1% DMSO could be from 0.04 to 0.06.

The OD level of the DMSO control was set as 100%; and the OD level of the test compound at different concentrations was determined. From the OD level at each concentration, Emax (%) and EC50 (μM) were computed and used as the index of the GK-activating potency of the compound.

The GK activating effect of the compounds of the invention was measured according to the method as above, and the results are shown in Table 5 below.

TABLE 5

| Example | Enantiomer | Emax(%) | EC50(uM) |
|---|---|---|---|
| 1 | A | 541 | 1.91 |
|   | B | 588 | 0.24 |
| 2 | A | 476 | 15.1 |
|   | B | 704 | 0.31 |
| 4 | A | 432 | 15.9 |
|   | B | 668 | 0.28 |
| 6 | A | 553 | 1.83 |
|   | B | 781 | 0.24 |
| 7 | A | 775 | 2.47 |
|   | B | 972 | 0.29 |
| 11 | A | 412 | 16.6 |
|   | B | 788 | 0.27 |

As shown in Table 5, in the compounds according to the present invention, the chiral benzimidazole compound has an excellent GK activating effect indicated by $E_{max}$ and $EC_{50}$ values.

The GK activating effect exhibited by the example compounds of WO 2007/007910 was measured by this method. The result of it compared to the compounds according to the present invention is shown in Table 6 described below.

TABLE 6

|  | Example No. |  | EC50(uM) |
|---|---|---|---|
| the present invention | 1 | Racemate | 0.53 |
|  | 7 | Racemate | 0.47 |
|  | 11 | Racemate | 0.49 |
| WO2007/007910 | 39 | Racemate | 1.87 |

As shown above, the compounds according to the present invention were improved in GK activating effect compared to that exhibited by the example compound of WO 2007/007910 by this method.

The antihyperglycemic effect of the compound according to the present invention, and a test method therefor are explained.

Pharmacological Test Example 2

Antihyperglycemic Effect

Six-week-old male C57BL/6J mice were fed a high-fat diet (RESEARCH DIETS, D12492) for ≥9 weeks to produce the high-fat diet loaded mice (>160 mg/dl).

The slight tail tips of the high-fat diet loaded mice (18-21 weeks old, n=6) under the conditions of free-feeding and water intake were cut with scissors to collect their blood. The collected blood was used to determine blood glucose levels prior to the administration of a compound by a blood glucose level measuring apparatus (One Touch Ultra (Johnson. Johnson)), followed by oral administration of the compound suspended in a 0.5% methyl cellulose solution at 10 mg/kg, while a 0.5% methyl cellulose solution was orally administered to the control group. The blood glucose levels were determined using the blood glucose level measuring apparatus every 1 hour after the administration of the test drug solutions.

The values of the decreases in blood glucose (differences between the control group and the compound-treated group) at 1 hour after administration were shown in Table 7 described below.

The values of the decreases in blood glucose (differences between the control group and the compound-treated group) at 1 hour after administration of the compounds according to Example 1 and Example 7 were shown in Table 7 described below.

TABLE 7

| Example: enantiomer | Difference from control group (Δmg/dl) |
|---|---|
| 1: B | −132 |
| 7: B | −146 |

Pharmacological Test Example 3

Antihyperglycemic Effect

From the cephalic vein of male beagles fasted overnight (9.4-14.4 kg body weight), blood was collected prior to administration, followed by oral administration of the test drug suspended in a 0.5% methyl cellulose solution (0.3 and 1 mg/kg), while a 0.5% methyl cellulose solution was orally administered to the control group. The blood was collected at 0.5, 1, 2, and 4 hours after the administration of the test drug. Plasma was separated from the obtained blood to determine a plasma glucose level using Determina-GL-E (Kyowa Medics).

Percentage reduction in plasma glucose level AUC compared to the control group up to 4 hours after the administration of the compounds according to Example 1 and Example 7 was described below.

TABLE 8

| Example | enantiomer | dose (mg/kg) | Rate of decrease (%) in plasma glucose level AUC |
|---|---|---|---|
| 1 | B | 0.3 | 16.2 |
|   |   | 1.0 | 23.4 |
| 7 | B | 0.3 | 12.4 |
|   |   | 1.0 | 15.6 |

This reveals that the compound according to the present invention has an excellent antihyperglycemic effect.

EFFECTS OF THE INVENTION

An oxotetrahydrofuran-2-yl-benzimidazole derivative according to the present invention of Formula (I) or a pharmaceutically acceptable salt thereof has a strong glucokinase-activating effect, and are useful for treatment and/or prevention of diabetes mellitus, diabetes mellitus complications, or obesity.

A compound according to the present invention is suitable for both types of diabetes mellitus, insulin-dependent diabetes mellitus (IDDM) and non-insulin dependent diabetes mellitus (NIDDM).

As used herein, a diabetes mellitus complication refers to a disease accompanying due to the onset of diabetes mellitus. Specifically, examples of diabetes mellitus complications include diabetic nephropathy, diabetic retinopathy, diabetic neuropathy, and diabetic arteriosclerosis.

BEST MODE FOR CARRYING OUT THE INVENTION

The present invention will now be explained in more detail referring to Formulation Examples, Examples, and Reference

17

Examples, with the understanding that the invention is in no way limited to these examples.

EXAMPLES

Formulation Example 1

10 parts of the compound of Production Example 1, 15 parts of heavy magnesium oxide and 75 parts of lactose are uniformly mixed to give a powdery or particulate preparation of at most 350 μm in size. The preparation is encapsulated to prepare capsules.

Formulation Example 2

45 parts of the compound of Production Example 1, 15 parts of starch, 16 parts of lactose, 21 parts of crystalline cellulose, 3 parts of polyvinyl alcohol and 30 parts of distilled water are uniformly mixed, then ground, granulated and dried, and thereafter sieved to prepare granules having a size of from 1410 to 177 μm in diameter.

Formulation Example 3

Granules are prepared in the same manner as in Preparation Example 2. 3 parts of calcium stearate is added to 96 parts of the granules, and shaped under compression to give tablets having a diameter of 10 mm.

Formulation Example 4

10 parts of crystalline cellulose and 3 parts of calcium stearate are added to 90 parts of the granules obtained according to the method of Preparation Example 2, and shaped under compression to give tablets having a diameter of 8 mm. These are coated with a mixture suspension of syrup gelatin and precipitated calcium carbonate to prepare sugar-coated tablets.

The thin-layer chromatography carried out in the examples employed Silicagel 60F245 (Merck) as a plate, in which amine thin-layer chromatography employed PLC05 NH (FUJI Silysia) as a plate and a UV detector was used as a detection method. The column silica gel used was Wakogel TMC-300 (Wako Pure Chemical Industries), Pulif-Pack SI or NH (Moritex), or FLASH cartridge (Biotage), and the reverse-phase column silica gel used was LC-SORBTMSP-B-ODS (Chemco) or YMC-GELTMODS-AQ120-S50 (Yamamura Kagaku Kenkyujo).

The abbreviations in the examples described below are described below.
i-Bu: isobutyl
n-Bu: n-butyl
t-Bu: t-butyl
Me: methyl
Et: ethyl
Ph: phenyl
i-Pr: isopropyl
n-Pr: n-propyl
CDC13: heavy chloroform
CD3OD: heavy methanol
DMSO-d6: heavy dimethylsulfoxide The abbreviations for nuclear magnetic resonance spectrum are described below.
s: singlet
d: doublet
dd: double doublet
dt: double triplet

18 t: triplet
m: multiplet
br: broad
brs: broad singlet
q: quartet
J: coupling constant
Hz: hertz Example 1

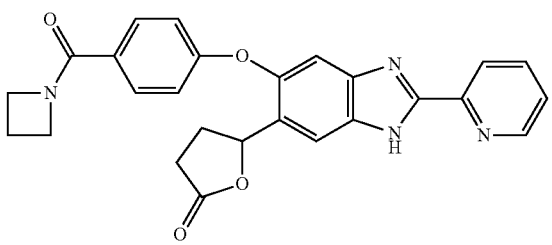

Formula

Preparation of 5-{5-[4-(azetidin-1-ylcarbonyl)phenoxy]-2-pyridin-2-yl-1H-benzimidazol-6-yl}dihydrofuran-2(3H)-one 1) 4-(azetidin-1-ylcarbamoyl)phenol (218 mg, 1.22 mmol) and cesium carbonate (991 mg, 3.04 mmol) were added to a N-methylpyrrolidone solution (8 ml) of N-[5-fluoro-2-nitro-4-(5-oxotetrahydrofuran-2-yl)phenyl]pyridine-2-carboxamide (350 mg, 1.01 mmol), produced by the method described in Steps 1 to 5 in Example 20 of WO 2007/007910, and this mixture was stirred for 1 hour at 120° C. under nitrogen atmosphere. This reaction solution was ice-cooled, followed by adding water to the reaction solution, filtering a precipitate, and drying the precipitate to obtain a brown solid containing N-[5-[4-(2-azetidin-1-yl-2-oxoethyl)phenoxy]-2-nitro-4-(5-oxotetrahydrofuran-2-yl)phenyl]pyridine-2-carboxamide.

2) Stannous chloride dihydrate (327 mg, 1.45 mmol) was added to a N,N-dimethylformamide (3 ml) solution of the compound obtained by the above-mentioned reaction, and this mixture was stirred for 4 hours at 100° C. This reaction solution was ice-cooled, followed by adding a saturated aqueous sodium bicarbonate solution and ethyl acetate to the reaction solution, extracting a water layer with ethyl acetate twice, washing the organic layer with a saturated aqueous sodium chloride solution, and drying over anhydrous sodium sulfate. This solvent was concentrated under reduced pressure, and the obtained residue was purified by thin-layer silica gel column chromatography (NH, 0.5 mm, chloroform:methanol=120:1) to obtain the racemate (87.0 mg, 0 mg, yield: 66%) of the title compound as a pale yellow solid.

3) The racemate (84 mg) obtained by the above-mentioned reaction was optically resolved by chiral column chromatography (Daicel CHIRALPAK AD-H (20*250 mm, 5 μm, 7 ml/min), hexane:isopropyl alcohol=30:70, 0.1% diethylamine) to obtain enantiomer A (faster: 22 min: 14 mg) of the title compound as a pale yellow solid and enantiomer B (slower: 36 min: 19 mg) as a pale yellow solid, respectively.

The analytical data of the title compound are shown below.

$^1$H-NMR (CDCl$_3$) δ: 2.14-2.40 (3H, m), 2.61-2.74 (3H, m), 4.22-4.35 (4H, m), 5.81 (1H, t, J=7.2 Hz), 6.99-7.04 (2.5H, m), 7.36-7.43 (1.5H, m), 7.62-7.66 (2.5H, m), 7.85-7.90 (1H, m), 7.93 (0.5H, s), 8.37 (0.5H, dd, J=0.8, 7.8 Hz), 8.41 (0.5H, dd, J=0.8, 7.8 Hz), 8.62 (0.5H, d, J=5.0 Hz), 8.66 (0.5H, d, J=5.0 Hz), 10.75 (0.5H, s), 10.82 (0.5H, s).

ESI-MS (m/e): 455 [M+H]$^+$

Preparation of 4-(azetidin-1-ylcarbonyl)phenol

1) Azetidine hydrochloride (10.3 g, 110 mmol), N-(3-dimethylaminopropyl)-N'-ethylcarbodiimide hydrochloride (25.2 g, 131 mmol), 1-hydroxybenzotriazole (20.1 g, 131 mmol), and triethylamine (33.6 ml, 241 mmol) were added to a N,N-dimethylformamide solution (500 ml) of 1-(benzyloxy)benzoate (25 g, 110 mmol), and this mixture was stirred overnight at room temperature. Water was added to this reaction solution, this mixture was extracted with ethyl acetate twice, followed by washing the organic layer with water and a saturated saline solution, drying the organic layer with anhydrous sodium sulfate, and thereafter concentrating this solvent under reduced pressure. The obtained residue was crystallized from chloroform-diethyl ether to obtain 1-[4-(benzyloxy)-benzoyl]azetidine (23.0 g, yield: 79%) as an ecru solid.

2) Following addition of palladium carbon (5 g, 50% wet, 47 mmol) to a tetrahydrofuran solution (400 ml) of the compound provided by the above-mentioned reaction, the reaction system was substituted by hydrogen and was stirred for 3 hours under 1 atmospheric pressure at room temperature. This reaction solution was filtered through Celite to remove the palladium carbon, and the solvent was concentrated under reduced pressure to obtain the title compound (15.1 g, yield: 100%) as a brown solid.

Example 2

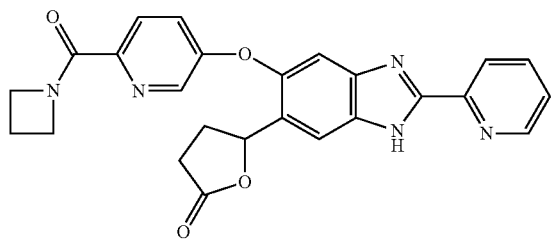

Formula

Preparation of 5-(5-{[6-(azetidin-1-ylcarbonyl)pyridin-3-yl)oxy}-2-pyridin-2-yl-1H-benzimidazol-6-yl)dihydrofuran-2(3H)-one The racemate of the title compound was obtained by the same method as in Example 1, a method similar thereto, or combinations of them and usual methods, using N-[5-fluoro-2-nitro-4-(5-oxotetrahydrofuran-2-yl)phenyl]pyridine-2-carboxamide and 6-(azetidin-1-ylcarbonyl)pyridin-3-ol, and then the racemate was optically resolved by optically active column chromatography (Daicel CHIRALPAK AD-H (20*250 mm, 5 μm), hexane:isopropyl alcohol=45:55, 0.1% diethylamine) to obtain enantiomer A (faster: 20 min: 24.0 mg) as a pale yellow solid and enantiomer B (slower: 35 min: 23.6 mg) as a pale yellow solid, respectively.

The analytical data of the title compound are shown below.

$^1$H-NMR (CDCl$_3$) δ: 2.15-2.40 (3H, m), 2.63-2.75 (3H, m), 4.25 (2H, t, J=7.6 Hz), 4.70 (2H, t, J=7.6 Hz), 5.81 (1H, t, J=7.2 Hz), 7.07 (0.5H, s), 7.34-7.43 (2.5H, m), 7.66 (0.5H, s), 7.85-7.91 (1H, m), 7.95 (0.5H, s), 8.09-8.13 (1H, m), 8.34-8.43 (2H, m), 8.62 (0.5H, d, J=4.5 Hz), 8.66 (0.5H, d, J=4.5 Hz), 10.77 (0.5H, s), 10.83 (0.5H, s).

ESI-MS (m/e): 456 [M+H]$^+$

Preparation of 6-(azetidin-1-ylcarbonyl)pyridin-3-ol

1) Palladium acetate (0.43 g, 1.89 mmol), 1,1'-bis(diphenylphosphino)ferrocene (2.10 g, 3.79 mmol), and triethylamine (11.1 ml, 80.0 mmol) were added to a methanol solution (200 ml) of 5-(benzyloxy)-2-bromopyridine (10.0 g, 37.8 mmol) under carbon monoxide atmosphere, this mixture was stirred for 2 days at 90° C. This reaction solution was cooled to room temperature, followed by concentrating this solvent under reduced pressure and purifying the obtained residue by silica gel column chromatography (Flash cartridge 65M, hexane:ethyl acetate=1:1) to obtain methyl 5-(benzyloxy)pyridine-2-carboxylate (7.48 g, yield: 81%) as an ecru solid.

2) Sodium hydroxide (4.14 g, 104 mmol) was added to a mixed solution of the compound obtained by the above-mentioned reaction (2.52 g, 10.35 mmol) of tetrahydrofuran (100 ml) and water (25 ml), and this mixture was stirred overnight at 60° C. This reaction solution was cooled to room temperature, followed by neutralizing the liquid with 4N hydrochloric acid and thereafter extracting the liquid with chloroform twice. The organic layer was dried over anhydrous sodium sulfate, followed by concentration under reduced pressure to obtain 5-(benzyloxy)pyridin-2-carboxylic acid (2.35 g, yield: 99%) as a white solid.

3) Azetidine (473 mg, 8.29 mmol), N-(3-dimethylaminopropyl)-N'-ethylcarbodiimide hydrochloride (1.74 g, 9.05 mmol), 1-hydroxybenzotriazole (1.39 g, 9.05 mmol), and triethylamine (2.31 ml, 16.6 mmol) were added to a N,N-dimethylformamide solution (40 ml) of the compound provided by the above-mentioned reaction (1.73 g, 7.54 mmol), and this mixture was stirred overnight at room temperature. Water was added to this reaction solution, and this mixture was extracted with ethyl acetate twice, followed by washing the organic layer with water and a saturated saline solution, drying the organic layer with anhydrous sodium sulfate, and thereafter concentrating this solvent under reduced pressure. The obtained residue was purified by silica gel column chromatography (Flash cartridge 40M, hexane:ethyl acetate=1:2) to obtain 2-(azetidin-1-ylcarbonyl)-5-(benzyloxy)pyridine (1.99 g, yield: 98%) as a pale yellow solid.

4) Palladium on carbon (400 mg, 50% wet, 3.76 mmol) was added to a tetrahydrofuran solution (45 ml) of the compound provided by the above-mentioned reaction, and this mixture was stirred for 3 hours under hydrogen atmosphere (1 atmospheric pressure) at room temperature. This reaction solution was filtered through Celite to remove the palladium carbon, and the solvent was concentrated under reduced pressure to obtain the title compound (1.43 g, yield: 100%) as a brown solid.

Example 3

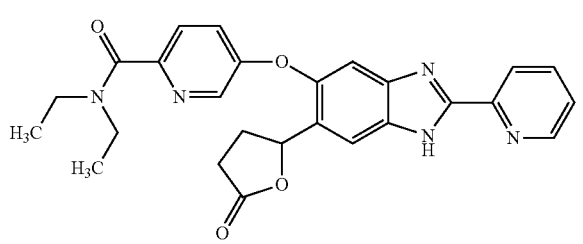

Formula 5

Preparation of N,N-diethyl-5-{[6-(5-oxotetrahydro-furan-2-yl)-2-pyridin-2-yl-1H-benzimidazol-5-yl]oxy}pyridine-2-carboxamide The racemate of the title compound was obtained by the same method as in Example 1, a method similar thereto, or combinations of them and usual methods, using N-[5-fluoro-2-nitro-4-(5-oxotetrahydrofuran-2-yl)phenyl]pyridine-2-carboxamide and N,N-diethyl-5-hydroxypyridine-2-carboxamide, and then the racemate was optically resolved by optically active column chromatography (Daicel CHIRALPAK IA-H (20*250 mm, 5 μm, 7 ml/min), hexane:IPA=25:75, 0.1% diethylamine) to obtain enantiomer A (faster: 20 min: 10.0 mg) as a pale yellow solid and enantiomer B (slower: 26 min: 10.0 mg) as a pale yellow solid, respectively.

The analytical data of the title compound are shown below.
$^1$H-NMR (DMSO-D$_6$) δ: 1.13-1.20 (6H, m), 2.20-2.36 (2H, m), 2.54-2.77 (4H, m), 3.48 (2H, d, J=7.0 Hz), 5.83-5.85 (1H, m), 7.15 (1H, s), 7.49-7.64 (4H, m), 7.91 (1H, brs), 8.04-8.06 (1H, m), 8.35-8.41 (2H, m), 8.80 (1H, s).
ESI-MS (m/e): 472 [M+H]$^+$

Preparation of N,N-diethyl-5-hydroxypyridine-2-carboxamide

1) Sodium pentoxide (0.58 mg, 5.24 mmol) was added to a N,N-dimethylformamide solution (44 mL) of 5-bromo-2-(ethylamide)pyridine (1.00 g, 4.37 mmol), this mixture was stirred for 15 minutes, ethyl iodide (1.02 g, 6.55 mol) was further added to the mixture, and the mixture was stirred overnight at room temperature. A Saturated aqueous sodium bicarbonate solution and ethyl acetate were added to this reaction solution, and the organic layer was washed with a saturated saline solution and dried over anhydrous sodium sulfate, followed by concentrating this solvent under reduced pressure. The obtained residue was purified by silica gel column chromatography (Purif-Pack SI60, hexane:ethyl acetate=1:1) to obtain 5-(benzyloxy)-2-(diethylamide)pyridine (390 mg, yield: 35%) as a pale yellow syrup.

2) Bis(pinacolate)diboron (424 mg, 1.67 mmol), palladium acetate (17.0 mg, 0.076 mmol), 1,1'-bis(diphenylphosphino)ferrocene (84 mg, 0.15 mmol), and potassium acetate (179 mg, 1.82 mmol) were added to 1,4-dioxane solution (15 mL) of the compound provided by the above-mentioned reaction, and this mixture was stirred overnight at 110° C. under nitrogen atmosphere. This reaction solution was cooled to room temperature, followed by Celite filtration of the reaction solution and thereafter concentrating it under reduced pressure.

3) 35% hydrogen peroxide water (0.17 mL, 1.97 mmol) was added dropwise to a tetrahydrofuran solution (3 mL) of the crude product provided by the above-mentioned reaction. The solution was stirred for 1 hour, followed by adding ethyl acetate (10 mL), washing the organic layer with an aqueous 5% sodium thiosulfate solution and water, thereafter drying the layer with anhydrous sodium sulfate, and distilling this solvent away under reduced pressure. The obtained residue was purified by silica gel column chromatography (Purif-Pack SI60, hexane:ethyl acetate=1:1) to obtain the title compound (250 mg, yield: 85%) as a pale yellow solid.

Example 4

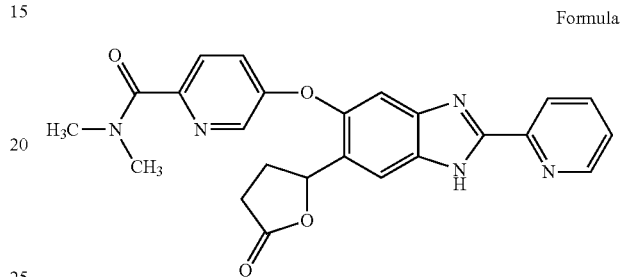

Formula

Preparation of N,N-dimethyl-5-{[6-(5-oxotetrahydrofuran-2-yl)-2-pyridin-2-yl-1H-benzimidazol-5-yl]oxy}pyridine-2-carboxamide The racemate of the title compound was obtained by the same method as in Example 1, a method similar thereto, or combinations of them and usual methods, using N-[5-fluoro-2-nitro-4-(5-oxotetrahydrofuran-2-yl)phenyl]pyridine-2-carboxamide and 5-hydroxy-N,N-dimethylpyridine-2-carboxamide, and then the racemate was optically resolved by optically active column chromatography (Daicel CHIRALPAK AD-H (20*250 mm, 5 μm, 10 ml/min), hexane:IPA=45:55, 0.1% diethylamine) to obtain enantiomer A (faster: 20 min: 47.0 mg) as a pale yellow solid and enantiomer B (slower: 27 min: 45.0 mg) as a pale yellow solid, respectively.

The analytical data of the title compound are shown below.
$^1$H-NMR (CDCl$_3$) δ: 2.12-2.36 (1H, m), 2.66-2.72 (3H, m), 3.15 (6H, s), 5.81 (1H, dd, J=5.1, 9.4 Hz), 7.31-7.41 (3H, m), 7.65 (2H, t, J=16.8 Hz), 7.85-7.93 (2H, m), 8.39 (2H, ddd, J=4.0, 7.9, 13.2 Hz), 8.63 (1H, dd, J=4.7, 12.9 Hz).
ESI-MS (m/e): 444 [M+H]$^+$

Preparation of 5-hydroxy-N,N-dimethylpyridine-2-carboxamide

1) A tetrahydrofuran solution of dimethylamine (2M, 3.30 mL) and N-(3-dimethylaminopropyl)-N'-ethylcarbodiimide hydrochloride (1.30 g, 6.50 mmol) were added to pyridine (10 ml) of 5-benzyloxy-2-carboxylic acid (500 mg, 2.20 mmol), and this mixture was stirred overnight at room temperature. The residue provided by concentrating the reaction solution under reduced pressure was dissolved in ethyl acetate, washed with an aqueous 10% citric acid solution, water and a saturated aqueous sodium bicarbonate solution, and dehydrated with anhydrous sodium sulfate, followed by concentration under reduced pressure. The obtained residue was purified by silica gel column chromatography (Purif-Pack SI60, hexane:ethyl acetate=1:1) to obtain 5-(benzyloxy)-2-(diethylamide)pyridine (517 mg, yield: 92%) as a pale yellow syrup.

2) The compound provided by the above-mentioned reaction was dissolved in 1,4-dioxan (5 mL), palladium hydroxide (100 mg, 0.7 mmol) was added to this mixture, and the mixture was intensely stirred for 2 hours under hydrogen atmosphere (1 atmospheric pressure). This reaction solution was filtered through Celite, followed by concentrating the solution. The obtained residue was purified by silica gel column chromatography (Purif-Pack SI60, chloroform:methanol=10:1) to obtain the title compound (312 mg, yield: 93%) as a pale yellow syrup.

Example 5

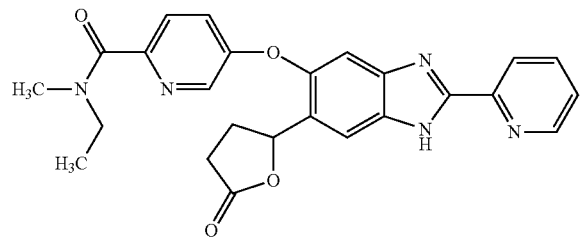

Formula

Preparation of N-ethyl-N-methyl-5-{[6-(5-oxotetrahydrofuran-2-yl)-2-pyridin-2-yl-1H-benzimidazol-5-yl]oxy}pyridine-2-carboxamide The racemate of the title compound was obtained by the same method as in Example 1, a method similar thereto, or combinations of them and usual methods, using N-[5-fluoro-2-nitro-4-(5-oxotetrahydrofuran-2-yl)phenyl]pyridine-2-carboxamide and 5-hydroxy-N,N-dimethylpyridine-2-carboxamide, and then the racemate was optically resolved by optically active column chromatography (Daicel CHIRALPAK AD-H (20*250 mm, 5 μm), hexane:EtOH=25:75, 0.1% diethylamine, 7 ml/min) to obtain enantiomer A (faster: 31 min: 60.0 mg) as a pale red solid and enantiomer B (slower: 36 min: 60 mg) as a pale red solid, respectively.

The analytical data of the title compound are shown below.
$^1$H-NMR (CDCl$_3$) δ: 1.18-1.23 (3H, brm), 2.14-2.29 (1H, m), 2.64-2.66 (3H, brm), 3.10 (3H, s), 3.59-3.61 (2H, m), 5.78 (1H, brs), 7.29 (1H, d, J=2.0 Hz), 7.33 (3H, dd, J=5.5, 13.7 Hz), 7.53-7.61 (1H, m), 7.78-7.90 (2H, m), 8.22-8.38 (2H, m), 8.58 (1H, s).
ESI-MS (m/e): 458 [M+H]$^+$ Preparation of
N-ethyl-5-hydroxy-N-methylpyridine-2-carboxamide 1) A tetrahydrofuran solution of ethylamine (2M, 3.27 mL) and N-(3-dimethylaminopropyl)-N'-ethylcarbodiimide hydrochloride (1.25 g, 6.54 mmol) were added to pyridine (10 ml) of 5-benzyloxy-2-carboxylic acid (500 mg, 2.18 mmol), and this mixture was stirred overnight at room temperature. The residue provided by concentrating the reaction solution under reduced pressure was dissolved in ethyl acetate, washed with an aqueous 10% citric acid solution, water and a saturated aqueous sodium bicarbonate solution, and dehydrated with anhydrous sodium sulfate, followed by concentration under reduced pressure. The obtained residue was purified by silica gel column chromatography (Purif-Pack SI60, hexane:ethyl acetate=1:1) to obtain 5-(benzyloxy)-2-(diethylamide)pyridine (210 mg, yield: 38%) as a pale yellow syrup.

2) Sodium hydride (32.8 mg, 0.82 mmol) was added to a N,N-dimethylformamide (8 ml) solution of the compound provided by the above-mentioned reaction at room temperature and this mixture was stirred for 15 minutes, followed by adding methyl iodide (233 mg, 1.6 mmol) to the mixture and stirring the mixture for 1 hour. A saturated aqueous sodium bicarbonate solution and ethyl acetate were added to this reaction solution, and the organic layer was washed with a saturated saline solution and dried over anhydrous sodium sulfate, followed by concentration under reduced pressure. The obtained residue was purified by silica gel column chromatography (Purif-Pack S160, chloroform:methanol=10:1) to obtain 5-(benzyloxy)-2-(diethylamide)pyridine (221 mg, yield: 100%) as a pale yellow syrup.

3) The compound provided by the above-mentioned reaction was dissolved in 1,4-dioxan (5 mL), palladium hydroxide (115 mg, 0.82 mmol) was added to this mixture, and the mixture was intensely stirred for 2 hours under hydrogen atmosphere. This reaction mixture was filtered through Celite, followed by concentrating the solution. The obtained residue was purified by silica gel column chromatography (Purif-Pack SI60, chloroform:methanol=10:1) to obtain the title compound (221 mg, yield: 100%) as a pale yellow syrup.

Example 6

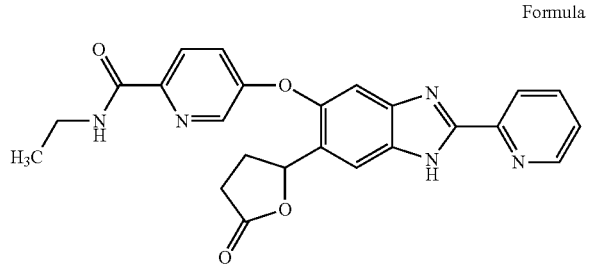 [SMILES: CCNC(=O)c1ccc(Oc2cc3nc(-c4ccccn4)[nH]c3cc2C2CCC(=O)O2)cn1]

Formula

Preparation of N-ethyl-5-{[6-(5-oxotetrahydrofuran-2-yl)-2-pyridin-2-yl-1H-benzimidazol-5-yl]oxy}pyridine-2-carboxamide The racemate of the title compound was obtained by the same method as in Example 1, a method similar thereto, or combinations of them and usual methods, using N-[5-fluoro-2-nitro-4-(5-oxotetrahydrofuran-2-yl)phenyl]pyridine-2-carboxamide and N-ethyl-5-hydroxypyridine-2-carboxamide, and then the racemate was optically resolved by optically active column chromatography (Daicel CHIRALPAK AD-H (20*250 mm, 5 μm), hexane:IPA=25:75, 0.1% diethylamine, 12 ml/min) to obtain enantiomer A (faster: 13 min: 150 mg) as a pale red solid and enantiomer B (slower: 24 min: 150 mg) as a pale red solid, respectively.

The analytical data of the title compound are shown below.
$^1$H-NMR (CDCl$_3$) δ: 1.26 (3H, t, J=7.2 Hz), 2.65-2.68 (4H, m), 3.52 (2H, dt, J=7.2, 14.1 Hz), 5.79 (1H, t, J=7.2 Hz), 7.38 (3H, ddd, J=2.9, 6.6, 12.5 Hz), 7.89 (2H, dq, J=3.7, 16.0 Hz), 8.18 (1H, d, J=9.0 Hz), 8.32 (1H, d, J=2.7 Hz), 8.41 (1H, d, J=7.8 Hz), 8.62 (1H, d, J=3.5 Hz).
ESI-MS (m/e): 444 [M+H]$^+$ Preparation of
N-ethyl-5-hydroxypyridine-2-carboxamide 1) A tetrahydrofuran solution of ethylamine (2M, 24.3 mL), hydroxybenzotriazole hydrate (9.29 g, 60.6 mmol), triethylamine (20.3 ml, 146 mmol), and N-(3-dimethylaminopropyl)-N'-ethylcarbodiimide hydrochloride (11.6 g, 60.6 mmol) were added to a mixed solution of tetrahydrofuran (200 ml) of 5-bromopyridine-2-carboxylic acid (4.90 g, 24.3 mmol) with water (50 ml), and this mixture was stirred overnight at 50° C. This reaction solution was concentrated, the residue was dissolved in ethyl acetate, and washed with an aqueous 10% citric acid solution, water and a saturated aqueous sodium bicarbonate solution, and dehydrated with anhydrous sodium sulfate, followed by concentration under reduced pressure, to obtain a crude product containing 5-bromo-2-(ethylamide)pyridine.

2) Bis(pinacolate)diboron (3.29 g, 13.0 mmol), palladium acetate (0.13 g, 0.59 mmol), 1,1'-bis(diphenylphosphino)ferrocene (0.65 g, 1.18 mmol), and potassium acetate (0.65 g, 1.18 mmol) were added to 1,4-dioxane solution (118 mL) of the compound provided by the above-mentioned reaction, and this mixture was stirred overnight at 110° C. under nitrogen atmosphere. This reaction solution was cooled to room temperature, followed by Celite filtration of the reaction solution and thereafter concentrating it under reduced pressure.

3) The compound provided by the above-mentioned reaction was dissolved in tetrahydrofuran (47 mL), and 35% hydrogen peroxide water (1.3 mL, 15 mmol) was added dropwise to this solution. The solution was stirred for 1 hour, followed by concentrating this reaction solution to 10 mL and adding chloroform (50 mL) to the solution. The organic layer was washed with an aqueous 5% sodium thiosulfate solution and water, followed by drying the layer with anhydrous sodium sulfate and distilling this solvent away under reduced pressure. The obtained residue was purified by silica gel column chromatography (Purif-Pack S1200, hexane:ethyl acetate=1:1) to obtain the title compound (1.10 g, yield: 56%) as a white solid.

Example 7

Formula

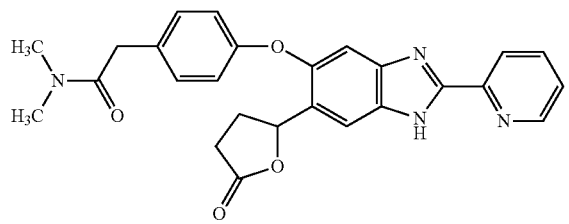

Preparation of N,N-dimethyl-2-(4-{[6-(5-oxotetrahydrofuran-2-yl)-2-pyridin-2-yl-1H-benzimidazol-5-yl]oxy}phenyl)acetamide 1) 2-(4-hydroxyphenyl)-N,N-dimethylacetamide (218 mg, 1.22 mmol) and cesium carbonate (991 mg, 3.04 mmol) were added to a N-methylpyrrolidone solution (8 ml) of N-[5-fluoro-2-nitro-4-(5-oxotetrahydrofuran-2-yl)phenyl]pyridine-2-carboxamide (350 mg, 1.01 mmol), and this mixture was stirred for 1 hour at 120° C. under nitrogen atmosphere. This reaction solution was ice-cooled, followed by adding water to the reaction solution, filtering a precipitate, and drying the precipitate to obtain a brown solid containing N-[5-[4-(2-dimethylamino-2-oxoethyl)phenoxy]-2-nitro-4-(5-oxotetrahydrofuran-2-yl)phenyl]pyridine-2-carboxamide.

2) Stannous chloride dihydrate (1.14 g, 5.07 mmol) was added to a N,N-dimethylformamide (8 ml) solution of the compound obtained by the above-mentioned reaction, and this mixture was stirred for 4 hours at 100° C. This reaction solution was ice-cooled, followed by adding a saturated aqueous sodium bicarbonate solution and ethyl acetate to the reaction solution, extracting a water layer with ethyl acetate twice, washing the organic layer with a saturated aqueous sodium chloride solution, and drying the organic layer with anhydrous sodium sulfate. This solvent was concentrated under reduced pressure, and the obtained residue was purified by thin-layer silica gel column chromatography (NH, 0.5 mm, chloroform:methanol=120:1) to obtain the racemate (351 mg, yield: 76%) of the title compound as a pale yellow solid.

3) The racemate (120 mg) obtained by the above-mentioned reaction was optically resolved by optically active column chromatography (Daicel CHIRALPAK AD-H (20*250 mm, 5 µm), hexane: isopropyl alcohol=30:70, 0.1% diethylamine) to obtain enantiomer A (faster: 23 min: 53.0 mg) of the title compound as a pale yellow solid and enantiomer B (slower: 28 min: 52.0 mg) as a pale yellow solid, respectively.

The analytical data of the title compound are shown below.

$^1$H-NMR (CDCl$_3$) δ: 2.12-2.31 (1H, m), 2.58-2.78 (3H, m) 2.95 (1.5H, s), 2.96 (1.5H, s), 3.00 (1.5H, s), 3.03 (1.5H, s), 3.67 (2H, d, J=3.1 Hz), 5.84 (1H, td, J=3.4, 7.0 Hz), 6.92-6.95 (2.5H, m), 7.18-7.23 (2H, m) 7.29-7.36 (1.5H, m), 7.56 (0.5H, s), 7.79-7.86 (1.5H, m), 8.31 (0.5H, d, J=8.0 Hz), 8.35 (0.5H, d, J=8.0 Hz), 8.57 (0.5H, d, J=4.5 Hz), 8.61 (0.5H, d, J=4.5 Hz), 10.54 (0.5H, s), 10.61 (0.5H, s).

ESI-MS (m/e): 457 [M+H]$^+$

Preparation of
2-(4-hydroxyphenyl)-N,N-dimethylacetamide

Dimethylamine hydrochloride (3.01 g, 36.9 mmol), N-(3-dimethylaminopropyl)-N'-ethylcarbodiimide hydrochloride (7.73 g, 40.3 mmol), 1-hydroxybenzotriazole (6.17 g, 40.3 mmol), and triethylamine (7.63 ml, 43.7 mmol) were added to a N,N-dimethylformamide solution (120 ml) of 4-(hydroxyphenyl)acetic acid (5.11 g, 33.6 mmol), and this mixture was stirred overnight at room temperature. Water was added to the reaction solution and the solution was extracted with chloroform twice, followed by drying the organic layer with anhydrous sodium sulfate and concentrating under reduced pressure. The obtained residue was crystallized from chloroform-diethyl ether to obtain the title compound (3.24 g, yield: 54%) as a white solid.

Example 8

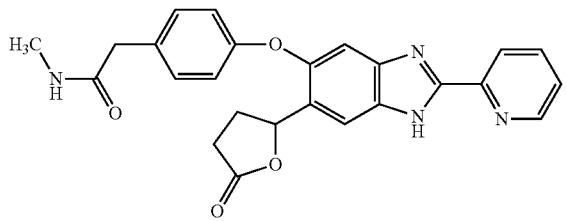

Formula 5

Preparation of N-methyl-2-(4-{[6-(5-oxotetrahydrofuran-2-yl)-2-pyridin-2-yl-1H-benzimidazol-5-yl]oxy}phenyl)acetamide The racemate of the title compound was obtained by the same method as in Example 7, a method similar thereto, or combinations of them and usual methods, using N-[5-fluoro-2-nitro-4-(5-oxotetrahydrofuran-2-yl)phenyl]pyridine-2-carboxamide and 2-(4-hydroxyphenyl)-N-methylacetamide, and then the racemate was optically resolved by optically active column chromatography (Daicel CHIRALPAK AD-H (20*250 mm, 5 μm), hexane:isopropanol=70:30, 12.5 ml/min) to obtain enantiomer A (faster: 14 min: 42 mg) as a white solid and enantiomer B (slower: 26 min: 36 mg) as a white solid, respectively.

The analytical data of the title compound are shown below.
$^1$H-NMR (CDCl$_3$) δ: 2.17-2.36 (1H, m), 2.54-2.75 (3H, m) 2.76 (1.5H, s), 2.77 (1.5H, s), 3.52 (2H, s), 5.48 (0.5H, brs), 5.70 (0.5H, brs), 5.80 (1H, q, J=7.4 Hz), 6.81 (0.5H, s), 6.90-6.96 (2H, m), 7.17-7.21 (2H, m) 7.31-7.37 (1.5H, m), 7.54 (0.5H, s), 7.79-7.84 (1.5H, m), 8.32 (0.5H, d, J=8.0 Hz), 8.36 (0.5H, d, J=8.0 Hz), 8.58-8.62 (1H, m) 10.85 (0.5H, s), 10.95 (0.5H, s).
ESI-MS (m/e): 443 [M+H]$^+$

Preparation of 2-(4-hydroxyphenyl)-N-methylacetamide

Methylamine hydrochloride (134 mg, 1.98 mmol), N-(3-dimethylaminopropyl)-N'-ethylcarbodiimide hydrochloride (475 mg, 2.48 mmol), 1-hydroxybenzotriazole (379 mg, 2.48 mmol), and triethylamine (0.69 ml, 4.95 mmol) were added to a N,N-dimethylformamide solution (10 ml) of 4-(hydroxyphenyl)acetic acid (400 mg, 1.65 mmol), and this mixture was stirred overnight at room temperature.

Water was added to the reaction solution and the solution was extracted with chloroform twice, followed by drying the organic layer with anhydrous sodium sulfate and concentration under reduced pressure. The obtained residue was purified by silica gel column chromatography (Flash cartridge 25M, chloroform:methanol=9:1) to obtain 2-[4-(benzoyloxy)-phenyl]-N-methylacetamide (455 mg, yield: 100%) as a white solid.

2) Palladium on carbon (400 mg, 50% wet, 3.76 mmol) was added to a mixed solution of the compound (455 mg, 1.78 mmol) provided by the above-mentioned reaction with chloroform (1 ml) and methanol (10 ml), this mixture was stirred overnight under hydrogen atmosphere (1 atmospheric pressure) at room temperature.

This reaction solution was filtered through Celite to remove the palladium on carbon, and the solvent was concentrated under reduced pressure to obtain the title compound (330 mg, yield: 100%) as a green-brown solid.

Example 9

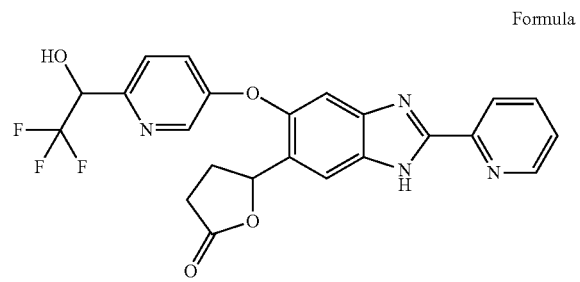 [SMILES: O=C1CCC(c2cc3[nH]c(-c4ccccn4)nc3cc2Oc2ccc(C(O)C(F)(F)F)nc2)O1]

Formula

Preparation of 5-(2-pyridin-2-yl-5-{[6-(2,2,2-trifluoro-1-hydroxyethyl)pyridin-3-yl]oxy}-1H-benzimidazole-6-yl)dihydrofuran-2(3H)-one The diastereo mixture of the racemate of the title compound was obtained by the same method as in Example 7, a method similar thereto, or combinations of them and usual methods, using N-[5-fluoro-2-nitro-4-(5-oxotetrahydrofuran-2-yl)phenyl]pyridine-2-carboxamide and 6-(2,2,2-trifluoro-1-hydroxyethyl)pyridin-3-ol. Subsequently, the racemate was optically resolved by optically active column chromatography (Daicel CHIRALPAK IA (20*250 mm, 5 μm, 10 ml/min), hexane:isopropanol=55:45, 0.1% diethylamine) to obtain the mixture of diastereomers A and B (faster: 15 min), diastereomer C (middle: 20 min: 2.2 mg) as a pale yellow solid, and diastereomer D (slower: 23 min: 3.0 mg) as a pale yellow solid, respectively.

The mixture of the diastereomers A and B provided as described above was further optically resolved by optically active column chromatography (Daicel CHIRALPAK OD-H (20*250 mm, 5 μm, 12.5 ml/min), hexane:isopropanol=70:30, 0.1% diethylamine) to obtain the diastereomers A of the title compound (faster: 22 min: 1.8 mg) and diastereomer B (slower: 26 min: 1.9 mg) as a pale yellow solid, respectively.

The analytical data of the title compound are shown below.
Diastereomers A and D
$^1$H-NMR (CDCl$_3$) δ: 2.24-2.32 (1.5H, m), 2.66-2.79 (3.5H, m), 5.04 (1H, s), 5.20 (1H, s), 5.81-5.86 (1H, m), 7.07 (0.5H, s), 7.26-7.27 (0.5H, m), 7.38-7.43 (3.5H, m), 7.67 (0.5H, s), 7.87-7.89 (1H, m), 8.37-8.45 (2H, m), 8.62-8.68 (1H, m), 10.58-10.62 (1H, m).
ESI-MS (m/e): 471 [M+H]$^+$
Diastereomers B and C
$^1$H-NMR (CDCl$_3$) δ: 2.20-2.24 (1H, m), 2.66-2.79 (4H, m), 5.04 (1H, s), 5.19 (1H, s), 5.84 (1H, t, J=6.8 Hz), 7.08 (0.5H, s), 7.38-7.41 (3H, m), 7.67 (0.5H, s), 7.87-7.89 (1.5H, m), 8.35-8.45 (2.5H, m), 8.64-8.67 (1H, m), 10.59-10.63 (1H, m).
ESI-MS (m/e): 471 [M+H]$^+$

Preparation of 6-(2,2,2-trifluoro-1-hydroxyethyl)pyridin-3-ol

Potassium carbonate (4.66 g, 36.3 mmol) was added to the mixture of pyridin-3-ol (2.00 g, 21.0 mmol) and 1-ethoxy-2,2,2-trifluoroethanol (3.30 g, 23.1 mmol), and the mixture was stirred for 4 hours at 100° C. under nitrogen atmosphere. This reaction solution was cooled to room temperature, followed by adding water and ethyl acetate to the reaction solution, washing the organic layer with a saturated saline solution, drying the layer with anhydrous sodium sulfate, and thereafter concentration under reduced pressure. The obtained residue was purified by silica gel column chromatography (Purif-Pack SI200, hexane:ethyl acetate:=40:60) to obtain the title compound (780 mg, yield: 19%) as a white amorphous.

Example 10

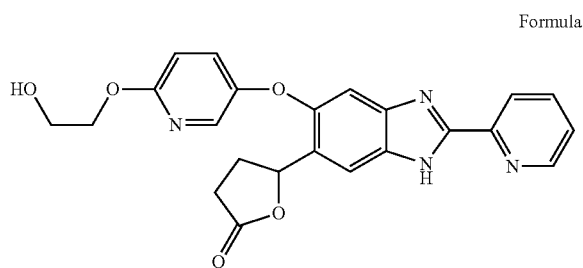 [SMILES: O=C1CCC(c2cc3[nH]c(-c4ccccn4)nc3cc2Oc2ccc(OCCO)nc2)O1]

Formula

Preparation of 5-(5-{[6-(2-hydroxyethoxy)pyridin-3-yl]oxy}-2-pyridin-2-yl-1H-benzimidazol-6-yl)dihydrofuran-2(3H)-one The racemate of the title compound was obtained by the same method as in Example 7, a method similar thereto, or combinations of them and usual methods, using N-[5-fluoro-2-nitro-4-(5-oxotetrahydrofuran-2-yl)phenyl]pyridine-2-carboxamide and 6-(2-hydroxyethoxy)pyridin-3-ol, and then the racemate was optically resolved by optically active column chromatography (Daicel CHIRALPAK IA-H (20*250 mm, 5 μm), hexane:IPA=40:60, 0.01% diethylamine, 8.5 ml/min) to obtain enantiomer A (faster: 15 min: 45 mg) as a pale yellow solid and enantiomer B (slower: 20 min: 46 mg) as a pale yellow solid, respectively.

The analytical data of the title compound are shown below.
$^1$H-NMR (CD$_3$OD) δ: 2.08 (1H, ddd, J=6.8, 10.4, 19.4 Hz), 2.42-2.72 (3H, m), 3.08-3.09 (1H, m), 3.67 (2H, t, J=4.9 Hz), 4.16 (2H, t, J=4.9 Hz), 5.80 (1H, t, J=7.6 Hz), 6.72 (1H, dd, J=2.7, 9.0 Hz), 6.87 (1H, t, J=10.2 Hz), 7.33-7.39 (1H, m), 7.43-7.47 (1H, m), 7.66 (1H, s), 7.78-7.83 (1H, m), 7.89 (1H, td, J=2.0, 7.8 Hz), 8.05 (1H, d, J=8.2 Hz), 8.62 (1H, dd, J=1.4, 4.5 Hz).
ESI-MS (m/e): 433 [M+H]$^+$ Preparation of 6-(2-hydroxyethoxy)pyridin-3-ol 1) Sodium hydride (1.97 mg, 82.0 mmol) was added to a N,N-dimethylformamide solution of 2-fluoro-5-bromopyridine (5.78 g, 32.9 mmol), and this mixture was stirred for 15 minutes. 2-benzyloxyethanol (5 g, 32.9 mmol) was added to the mixture, and the reaction mixture was stirred for additional 30 minutes at room temperature. A saturated aqueous sodium bicarbonate solution and ethyl acetate were added to this reaction solution, the organic layer was washed with a saturated saline solution and dried over anhydrous sodium sulfate, followed by concentrating this solvent under reduced pressure to obtain a crude product containing 2-[2-(benzyloxy)-ethoxy]-5-bromopyridine.

2) Bis(pinacolate)diboron (9.19 g, 36.2 mmol), palladium acetate (0.37 g, 1.64 mmol), 1,1'-bis(diphenylphosphino)ferrocene (1.82 g, 3.29 mmol), and potassium acetate (3.87 g, 39.5 mmol) were added to 1,4-dioxane solution (66 mL) of the compound provided by the above-mentioned reaction, and this mixture was stirred overnight at 110° C. under nitrogen atmosphere. This reaction solution was cooled to room temperature, followed by Celite filtration of the reaction solution and thereafter concentrating it under reduced pressure.

3) 35% hydrogen peroxide water (3.74 ml, 42.8 mmol) was slowly added to a tetrahydrofuran solution (66 ml) of the crude product provided by the above-mentioned reaction. This mixture was stirred for 1 hour, followed by concentrating the reaction solution to 10 mL under reduced pressure and adding ethyl acetate (60 mL) to the solution.

The organic layer was washed with an aqueous 5% sodium thiosulfate solution and water, followed by being dried over anhydrous sodium sulfate and distilling this solvent away under reduced pressure. The obtained residue was purified by silica gel column chromatography (Purif-Pack SI400, chloroform:methanol=10:1) to obtain 5-(hydroxy)-2-(benzyloxyethoxy)pyridine (5.17 g, yield: 64%) as a pale yellow solid.

4) The compound (1.2 g, 4.89 mmol) provided by the above-mentioned reaction was dissolved in 1,4-dioxane (50 mL), palladium hydroxide (250 mg, 1.78 mmol) was added to this solution, and the solution was intensely stirred for 3 days under hydrogen atmosphere. Following Celite filtration of this reaction solution, the solution was concentrated to obtain the title compound (680 mg).

Example 11

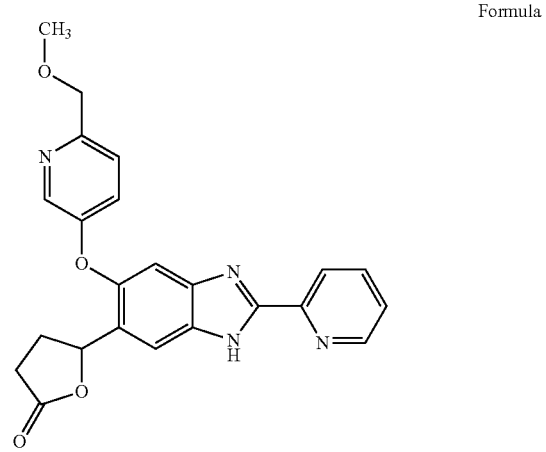 [SMILES: COCc1ccc(Oc2cc3nc(-c4ccccn4)[nH]c3cc2C2CCC(=O)O2)cn1]

Formula

Preparation of 5-(5-{[6-(methoxymethyl)pyridin-3-yl]oxy}-2-pyridin-2-yl-1H-benzimidazol-6-yl)dihydrofuran-2(3H)-one The racemate of the title compound was obtained by the same method as in Example 7, a method similar thereto, or combinations of them and usual methods, using N-[5-fluoro-2-nitro-4-(5-oxotetrahydrofuran-2-yl)phenyl]pyridine-2-carboxamide and 6-(methoxymethyl)pyridin-3-ol, and then the racemate was optically resolved by optically active column chromatography (Daicel CHIRALPAK AD-H (20*250 mm, 5 μm), hexane:ethanol=25:75, 0.1% diethylamine, 7 ml/min) to obtain enantiomer A (faster: 15 min: 28.2 mg) as a colorless solid and enantiomer B (slower: 29 min: 28.8 mg) as a colorless solid, respectively.

The analytical data of the title compound are shown below.

¹H-NMR (CDCl₃) δ: 2.19-2.34 (1H, m), 2.64-2.69 (2H, m), 2.72-2.81 (1H, m), 3.50 (3H, d, J=5.9 Hz), 4.59 (2H, d, J=2.4 Hz), 5.87 (1H, t, J=7.1 Hz), 6.96 (0.5H, s), 7.30-7.43 (3.5H, m), 7.62 (0.5H, s), 7.87 (1H, tdd, J=1.5, 3.5, 7.7 Hz), 7.93 (0.5H, s), 8.35-8.39 (1H, m), 8.42 (1H, t, J=2.0 Hz), 8.61-8.66 (1H, m), 10.64 (0.5H, s), 10.75 (0.5H, s)

ESI-MS (m/e): 417 [M+H]⁺

Preparation of 6-(methoxymethyl)pyridin-3-ol

1) Sodium hydride (4.76 g, 119 mmol) was added to a dimethylformamide solution (100 ml) of 6-methylpyridin-3-ol (10.0 g, 91.6 mmol) under ice cooling, and this mixture was stirred for 30 minutes, followed by adding benzyl chloride (12.7 ml, 110 mmol) to the mixture and stirring it for 12 hours at room temperature. Water and a saturated saline solution (1:1) and ethyl acetate were added to this reaction solution, and the solution was extracted. The organic layer was washed with water and a saturated saline solution, dried over anhydrous magnesium sulfate, and concentrated under reduced pressure. The obtained residue was purified by silica gel column chromatography (hexane:ethyl acetate=10:1 to 1:2) to obtain 5-(benzyloxy)-2-methylpyridine (16.4 g, yield: 90%) as an orange-colored product.

2) 3-chloroperbenzoic acid (28.1 g, 163 mmol) was added to a chloroform solution (300 ml) of the compound (16.4 g, 82.0 mmol), provided by the above-mentioned reaction, and sodium hydrogen carbonate (20.5 g, 244 mmol) under ice cooling, and this mixture was stirred for 1 hour at room temperature. Water was added to this reaction solution, and the solution was extracted. The organic layer was dried over anhydrous magnesium sulfate, followed by being concentrated under reduced pressure. The obtained residue was purified by silica gel chromatography (hexane:ethyl acetate=1:1, chloroform:methanol=20:1 to 10:1) to obtain 5-(benzyloxy)-2-methylpyridine-1-oxide (17.4 g, yield: 98%) as a colorless solid.

3) An acetic anhydride solution (500 ml) of the compound (17.2 g, 79.9 mmol) provided by the above-mentioned reaction was stirred for 30 minutes at 130° C. This reaction solution was concentrated under reduced pressure, followed by adding saturated sodium bicarbonate water and ethyl acetate to the liquid and extracting the liquid. The organic layer was dried over anhydrous magnesium sulfate, followed by being concentrated under reduced pressure. The obtained residue was purified by silica gel column chromatography (hexane:ethyl acetate=20:1 to 1:2) to obtain [5-(benzyloxy)-2-pyridin-2-yl]methyl acetate (16.2 g, yield: 79%) as an orange-colored product.

4) A 5N aqueous sodium hydroxide solution (25 ml, 125 mmol) was added to an ethanol solution (100 ml) of the compound (16.2 g, 63.0 mmol) provided by the above-mentioned reaction, and this mixture was stirred for 1 hour at 80° C. This reaction solution was concentrated under reduced pressure, followed by adding ethyl acetate to the solution and extracting the solution. The organic layer was dried over anhydrous magnesium sulfate, followed by being concentrated under reduced pressure. The obtained residue was purified by silica gel chromatography (hexane:ethyl acetate=3:1 to 1:2, ethyl acetate, chloroform:methanol=10:1) to obtain [5-(benzyloxy)-2-pyridin-2-yl]methanol (8.56 g, yield: 63%) as a pale yellow solid.

5) Sodium hydride (477 mg, 11.9 mmol) was added to a tetrahydrofuran solution (80 ml) of the compound (2.14 g, 9.94 mmol) provided by the above-mentioned reaction under ice cooling, and this mixtured was stirred for 30 minutes, followed by adding methyl iodide (681 μl, 10.9 mmol) to the mixture and further stirred it for 3 hours at room temperature. Water was added to this reaction solution, ethyl acetate was added to the solution, and the solution was extracted. The organic layer was dried over anhydrous magnesium sulfate, followed by being concentrated under reduced pressure. The obtained residue was purified by silica gel chromatography (hexane:ethyl acetate=3:1 to 1:1) to obtain 5-(benzyloxy)-2-(methoxymethyl)pyridine (2.02 g, yield: 88%) as a pale yellow oil.

6) 10% palladium on carbon (204 mg) was added to a methanol solution (40 ml) of the compound (2.02 g, 8.79 mmol) provided by the above-mentioned reaction, and this mixture was stirred for 1 hour at room temperature under hydrogen atmosphere. The reaction solution was filtered, followed by being concentrated under reduced pressure. The obtained residue was purified by silica gel chromatography (hexane:ethyl acetate=3:1 to ethyl acetate) to obtain the title compound (1.19 g, yield: 97%) as a colorless solid.

Example 12

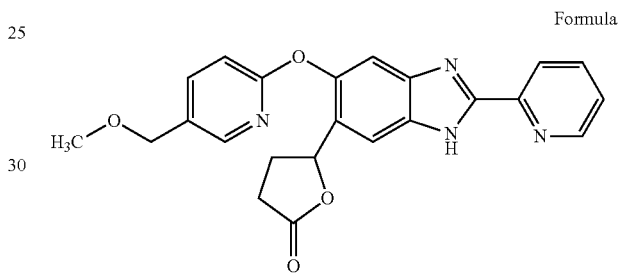

Formula

Preparation of 5-(5-{[5-(methoxymethyl)pyridin-2-yl]oxy}-2-pyridin-2-yl-1H-benzimidazole-6-yl)dihydrofuran-2(3H)-one The racemate of the title compound was obtained by the same method as in Example 7, a method similar thereto, or combinations of them and usual methods, using N-[5-fluoro-2-nitro-4-(5-oxotetrahydrofuran-2-yl)phenyl]pyridine-2-carboxamide and 5-(methoxymethyl)pyridin-2-ol, and then the racemate was optically resolved by optically active column chromatography (Daicel CHIRALPAK AD-H (20*250 mm, 5 μm), hexane:isopropyl alcohol=25:75, 7 ml/min) to obtain enantiomer A (faster: 14 min: 14 mg) as a white solid and enantiomer B (slower: 30 min: 14 mg) as a white solid, respectively.

The analytical data of the title compound are shown below.
¹H-NMR (CDCl₃) δ: 2.18-2.67 (4H, m), 3.41 (3H, s), 4.42 (2H, s), 5.72-5.85 (1H, brm), 6.96 (1H, brs), 7.31-7.93 (4H, m), 8.14 (1H, s), 8.38 (1H, brs), 8.56-8.69 (1H, brm), 10.58 (1H, brs).

ESI-MS (m/e): 417 [M+H]⁺

Preparation of 5-(methoxymethyl)pyridin-2-ol 1) 2-(trimethylsilyl)ethoxymethyl chloride (1.63 ml, 9.17 mmol) and 60% sodium hydride (0.45 g, 11.5 mmol) were added to a N,N-dimethylformamide solution (40 ml) of 6-oxy-1,6-dihydropyridine-3-methyl carboxylic acid (1.17 g, 7.64 mmol) under ice cooling, and this mixture was stirred for 1 hour at room temperature. Water and ethyl acetate were added to the reaction solution, and the organic layer was washed with a saturated aqueous ammonium chloride solution and a saturated saline solution and dried over anhydrous sodium sulfate, followed by being concentrated under reduced pressure. The obtained residue was purified by silica gel column chromatography (Purif-Pack SI60, hexane:ethyl acetate=19:1 to 1:1) to obtain 6-oxy-1-{[2-(trimethylsilyl)ethoxy)methyl}-1,6-dihydropyridine-3-methyl carboxylic acid (1.06 g, yield: 49%) as a colorless oil.

2) A 2N sodium hydroxide solution (5 ml) was added to a methanol solution (20 ml) of the compound (1.06 g, 3.74 mmol) provided by the above-mentioned reaction, this mixture was added for 1.5 hours at room temperature. 5N hydrochloric acid (2 ml) was added to the reaction solution, followed by distilling methanol away under reduced pressure and adding chloroform to the solution. The organic layer was washed with a saturated aqueous ammonium chloride solution and a saturated saline solution and dried over anhydrous sodium sulfate, followed by being concentrated under reduced pressure to obtain a crude product containing 6-oxy-1-{[2-(trimethylsilyl)ethoxy)methyl}-1,6-dihydropyridine-3-methyl carboxylic acid.

3) 1,1'-carbonyldiimidazole (0.90 g, 5.57 mmol) was added to a tetrahydrofuran solution (20 ml) of the compound provided by the above-mentioned reaction, and this mixture was stirred for 6 hours at room temperature. A 5.6M aqueous sodium borohydride solution (10 ml, 5.6 mmol) was added to the reaction solution under ice cooling, and this mixture was further stirred for 30 minutes. A saturated aqueous ammonium chloride solution and chloroform were added to the reaction solution, and the organic layer was washed with a saturated saline solution and dried over anhydrous sodium sulfate, followed by being concentrated under reduced pressure. The obtained residue was purified by silica gel chromatography (Purif-Pack SI60, chloroform:methanol=99.6:0.4 to 96:4) to obtain 5-(hydroxymethyl)-1-{[2-(trimethylsilyl)ethoxy]methyl)pyridin-2(1H)-one (794 mg, yield: 84%) as a colorless oil.

4) Methyl iodide (0.97 ml, 15.6 mmol) and 60% sodium hydride (497 mg, 12.4 mmol) were added to a tetrahydrofuran solution (20 ml) of the compound (794 mg, 3.11 mmol), provided by the above-mentioned reaction, under ice cooling, and this mixture was stirred for 6 hours at room temperature. A saturated aqueous ammonium chloride solution and ethyl acetate were added to the reaction solution, and the organic layer was washed with a saturated saline solution and dried over anhydrous magnesium sulfate, followed by being concentrated under reduced pressure. The obtained residue was purified by silica gel chromatography (Purif-Pack SI60, chloroform:methanol=99.8:0.2 to 98:2) to obtain 5-(methoxymethyl)-1-{[2-(trimethylsilyl)ethoxy]methyl}pyridin-2(1H)-one (488 mg, yield: 58%) as a colorless oil.

5) Trifluoroacetic acid (5 ml) was added to a chloroform solution (15 ml) of the compound (488 mg, 1.81 mmol) provided by the above-mentioned reaction, and this mixture was stirred for 3 hours at room temperature. The reaction solution was concentrated under reduced pressure, followed by purifying the obtained residue by silica gel chromatography (Purif-Pack SI20, chloroform:methanol=99.4:0.6 to 94:6) to obtain the title compound (200 mg, yield: 79%) as a colorless crystal.

INDUSTRIAL APPLICABILITY

An oxotetrahydrofuran-2-yl-benzimidazole derivative according to the present invention of Formula (I) or a pharmaceutically acceptable salt thereof is useful in treatment and/or prevention of diabetes mellitus, diabetes mellitus complications or obesity in the pharmaceutical field because of exhibiting an excellent glucokinase-activating effect.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the subject or mammal being treated obesity, diabetes, obesity-related disorders, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and embodiments of the present invention. It is intended, therefore, that the invention be limited only by the scope of the claims which follow and that such claims be interpreted as broadly as is reasonable.

The invention claimed is:
1. A compound of formula (I), or a pharmaceutically acceptable salt thereof:

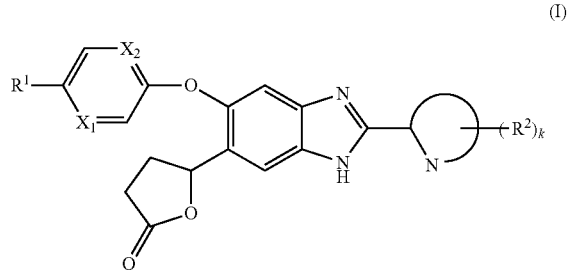

wherein $R^1$ is Formula (II):

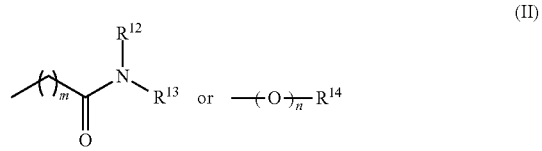

wherein $R^{12}$ and $R^{13}$ independently represent a hydrogen atom or a lower alkyl group;
$R^{14}$ represents a lower alkyl group optionally having 1 to 4, the same or different hydroxy groups, lower alkoxy groups or halogen atoms;
m represents zero or 1;
n represents zero or 1; and
both of $X_1$ and $X_2$ represent CH; and
a group of Formula (IV):

which represents a pyridinyl group;
R² represents a lower alkyl group optionally substituted with a hydroxy group, a lower alkoxy group, or a hydroxy group; and
k represents zero or 1.

2. The compound of claim 1 or a pharmaceutically acceptable salt thereof, wherein R¹ is a group of Formula (II-2):

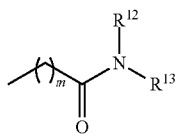

(II-2)

wherein each symbol has the meaning provided in claim 1.

3. The compound of claim 1 or a pharmaceutically acceptable salt thereof, wherein R¹ is a group of (II-3):

—R¹⁴ (II-3)

wherein each symbol has the meaning provided in claim 1.

4. The compound of claim for a pharmaceutically acceptable salt thereof, wherein R¹ is a methoxymethyl group.

5. The compound of claim 1 or a pharmaceutically acceptable salt thereof, wherein R¹ is a dimethylcarbamoylmethyl group or a methylcarbamoylmethyl group.

6. The compound of claim 1 or a pharmaceutically acceptable salt thereof, wherein m is 1.

7. The compound of claim 1 or a pharmaceutically acceptable salt thereof, wherein k is zero.

8. The compound according to claim 1 or a pharmaceutically acceptable salt thereof, wherein the compound of Formula (I) is selected from the group consisting of:
N,N-dimethyl-2-(4-{[6-(5-oxotetrahydrofuran-2-yl)-2-pyridin-2-yl-1H-benzimidazol-5-yl]oxy}phenyl)acetamide, and
N-methyl-2-(4-{[6-(5-oxotetrahydrofuran-2-yl)-2-pyridin-2-yl-1H-benzimidazol-5-yl]oxy}phenyl)acetamide.

9. A method for treating diabetes mellitus comprising administering a compound of claim 1 or a pharmaceutically acceptable salt thereof in an amount effective for the treatment of diabetes mellitus, and a pharmaceutically acceptable carrier.

10. A pharmaceutical composition comprising a compound of claim 1 or a pharmaceutically acceptable salt thereof and a pharmaceutically acceptable carrier.

* * * * *